United States Patent [19]

De Stefanis et al.

[11] 4,299,848
[45] Nov. 10, 1981

[54] MODIFIED ENZYME SYSTEM TO INHIBIT BREAD FIRMING METHOD FOR PREPARING SAME AND USE OF SAME IN BREAD AND OTHER BAKERY PRODUCTS

[75] Inventors: Vincent A. De Stefanis, White Plains; Earl W. Turner, Port Chester, both of N.Y.

[73] Assignee: International Telephone and Telegraph Corporation, New York, N.Y.

[21] Appl. No.: 46,876

[22] Filed: Jun. 8, 1979

[51] Int. Cl.³ .................. A21D 2/08; C12N 9/28; C12N 9/99
[52] U.S. Cl. .................. 426/20; 426/24; 426/26; 426/62; 426/64; 426/549; 426/558; 426/653; 435/184; 435/188; 435/202; 435/814; 435/816
[58] Field of Search ............. 426/20, 24, 26, 62, 426/64, 549, 558, 653, 430; 435/184, 188, 202, 814, 816, 815, 839; 195/66 R

[56] References Cited

U.S. PATENT DOCUMENTS

| | | | |
|---|---|---|---|
| Re. 28,074 | 7/1974 | Smerak et al. | 426/20 |
| 2,351,954 | 6/1944 | Gore et al. | 435/188 X |
| 2,615,810 | 10/1952 | Stone | 426/20 |
| 2,665,215 | 1/1954 | Gray | 426/20 |
| 2,683,682 | 7/1954 | Miller et al. | 435/184 |
| 2,979,440 | 4/1961 | Smythe | 426/188 X |
| 3,026,205 | 3/1962 | Stone | 426/64 X |
| 3,494,770 | 2/1970 | Smerak et al. | 426/20 |
| 3,527,644 | 9/1970 | Landfried et al. | 426/20 X |
| 3,592,737 | 7/1971 | Keay et al. | 435/202 |
| 3,826,715 | 7/1974 | Horikoshi et al. | 435/202 |
| 4,010,073 | 3/1977 | Drake | 435/187 |
| 4,160,848 | 7/1979 | Vidal et al. | 426/20 X |

FOREIGN PATENT DOCUMENTS 2735480  2/1978  Fed. Rep. of Germany.

OTHER PUBLICATIONS

Silverstein, *The Bakers Digest*, Aug. 1964, 66–72.
Harrell et al., *The Bakers Digest*, Dec. 1950, 19–22.
Waldt, *The Bakers Digest*, Oct. 1968, 64–66, 73.
Waldt et al., *Cereal Science Today*, 12(9), 358–362, 381 (1967).

*Primary Examiner*—Esther M. Kepplinger
*Attorney, Agent, or Firm*—John T. O'Halloran; David M. Quinlan

[57] ABSTRACT

A method to inactivate the proteolytic enzyme(s) contained in commercial heat stable bacterial alpha-amylase under conditions which retain full alpha-amylase activity. Use of thus purified alpha-amylase enzyme plus surfactants that are approved for use in bread to inhibit firming and improve the keeping quality of bread and other bakery products.

48 Claims, 8 Drawing Figures

10.0 g. of PBAA dissolved in 50 ml of 5% NaCl solution, followed by the addition of 50 ml of methanol or ethanol, then centrifuged at 3000 RPM for 5 minutes 50.0% methanol in 5.0% NaCl solution (v.)

↓ ↓

Solubles → increase MeOH concentration from 50.0% to 75.0% by volume, then centrifuge Insolubles → trace enzyme activity plus non-enzyme components Solubles — much color plus non-enzyme components were removed Insolubles — 95–97% of the original enzyme activity plus some color (enzyme to be used in baking).

FIG. 6

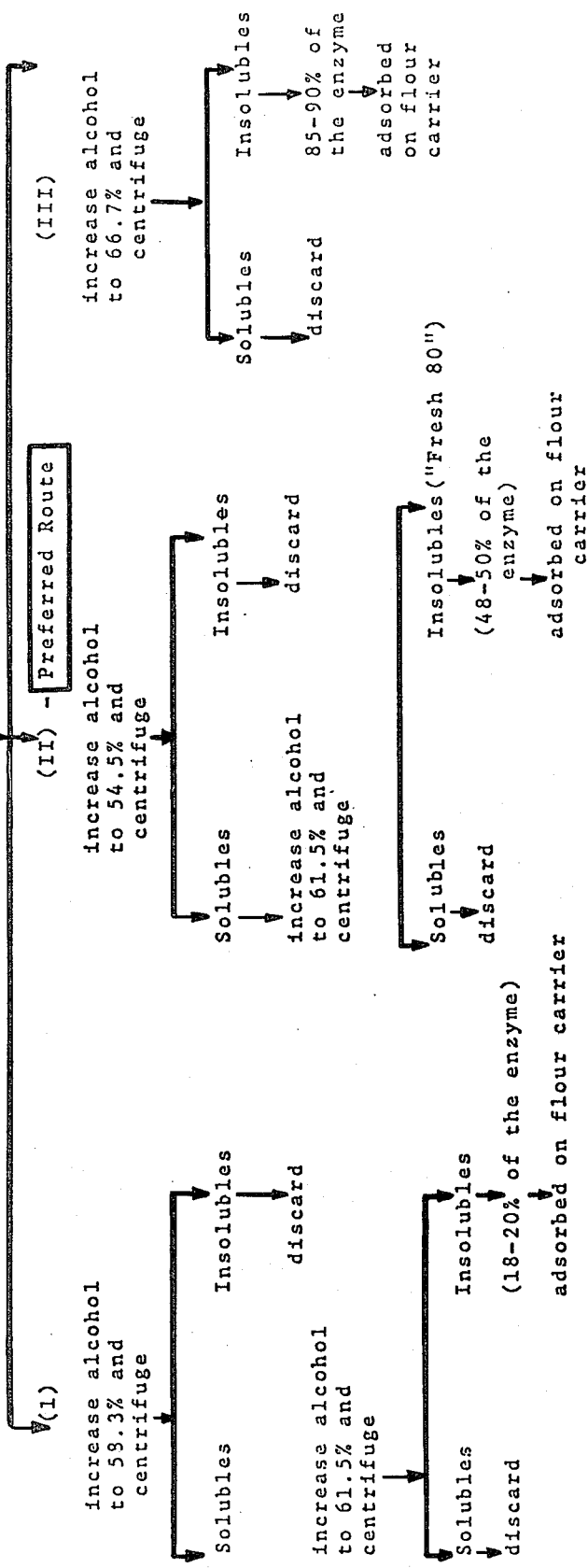

MODIFIED ENZYME SYSTEM TO INHIBIT BREAD FIRMING METHOD FOR PREPARING SAME AND USE OF SAME IN BREAD AND OTHER BAKERY PRODUCTS

BACKGROUND OF THE INVENTION

Market research has established that consumers select bread and similar bakery products based upon their fresh, soft texture. Staling is perceived by the development of a firm, dry texture which becomes noticeable within one or two days after baking, and results in a loss of product acceptability. Monoglycerides and other surfactant compounds are added to bread to achieve improved softness. Surfactants usage results in softer bread, but they do not materially affect the rate of bread firming.

Bread staling or firming is due primarily to changes, which occur in the starch fraction. The firming of bread crumb cannot be attributed to changes in moisture content, since the moisture content of one and six day old bread is essentially the same when the product is packaged to prevent moisture loss. Yet, the bread texture becomes increasingly firmer on storage, and is usually considered unacceptable after the fourth day. Evidence shows that amylose and amylopectin starch fractions retrograde or crystallize during bread storage to form a firm, dry texture. Starch makes up about 70 percent of the dry weight of bread, and evidence indicates that some of the textural changes, which are observed on staling, are due to crystallization of the starch components.

Since bread staling or firming is believed to be caused by crystallization of gelatinized starch, it would appear that these textural changes could be modified or inhibited by using starch hydrolyzing enzymes to fragment the starch polymers, thus reducing the degree of interaction or firming on storage. Attempts to use commercially available enzyme preparations, such as heat stable bacterial alpha-amylase enzyme have not met with success because the degree of enzyme action has been too difficult to control. Either the degree of enzyme action has been inadequate with little or no improvement in bread texture, and anti-firming properties, or when enough enzyme is added to obtain a softer texture, failures arise due to the formation of a very tacky, gummy bread crumb with a loss of load volume and destruction of bread quality.

It is the object of this invention to develop a heat stable enzyme system, which can be used to provide a controlled degree of alpha-amylase activity to inhibit the firming of bread and other bakery products, thus achieving a longer product storage life without loss of quality.

SUMMARY OF THE INVENTION

This invention relates to a process for the inactivation of the proteolytic enzyme(s), which are present in commercially available heat stable bacterial alpha-amylase enzyme preparations obtained from extracts of *Bacillus subtilis*, *Bacillus sterothermophilis* or other microbial sources. The proteolytic enzyme(s) in our embodiment are inactivated by heating the commercial enzyme preparations in buffer solutions under controlled conditions of time, temperature, pH, and specific ion concentrations. The proteolytic enzyme(s) are inactivated, and alpha-amylase activity is retained by the procedures used. The invention includes use of this heat stable alpha-amylase enzyme system purified to remove protease enzyme activity, either alone or in combination with effective levels of our approved surfactants to obtain a controlled degree of bread softness, and decrease in the rate of bread firming on storage, without loss of product quality. The activity of the purified enzyme system is standardized, and only low levels of enzyme activity are used to obtain the desired result.

BRIEF DESCRIPTION OF THE DRAWINGS

The novel features believed characteristic of the invention are set forth in the appended claims. The invention itself, however, as well as further objects and advantages thereof, will best be understood by reference to the following detailed description of an illustrated embodiment taken in conjunction with the accompanying drawings, in which:

FIGS. 6 and 7 are a process flow diagram for the "cleaning up" of purified bacterial alpha-amylase of Maxamyl and HT-concentrate, and FIG. 8 is a process flow diagram for a preferred commercial process for the purification and adsorption of the purified bacterial alpha-amylase on a flour carrier.

DETAILED DESCRIPTION

Figure 1:
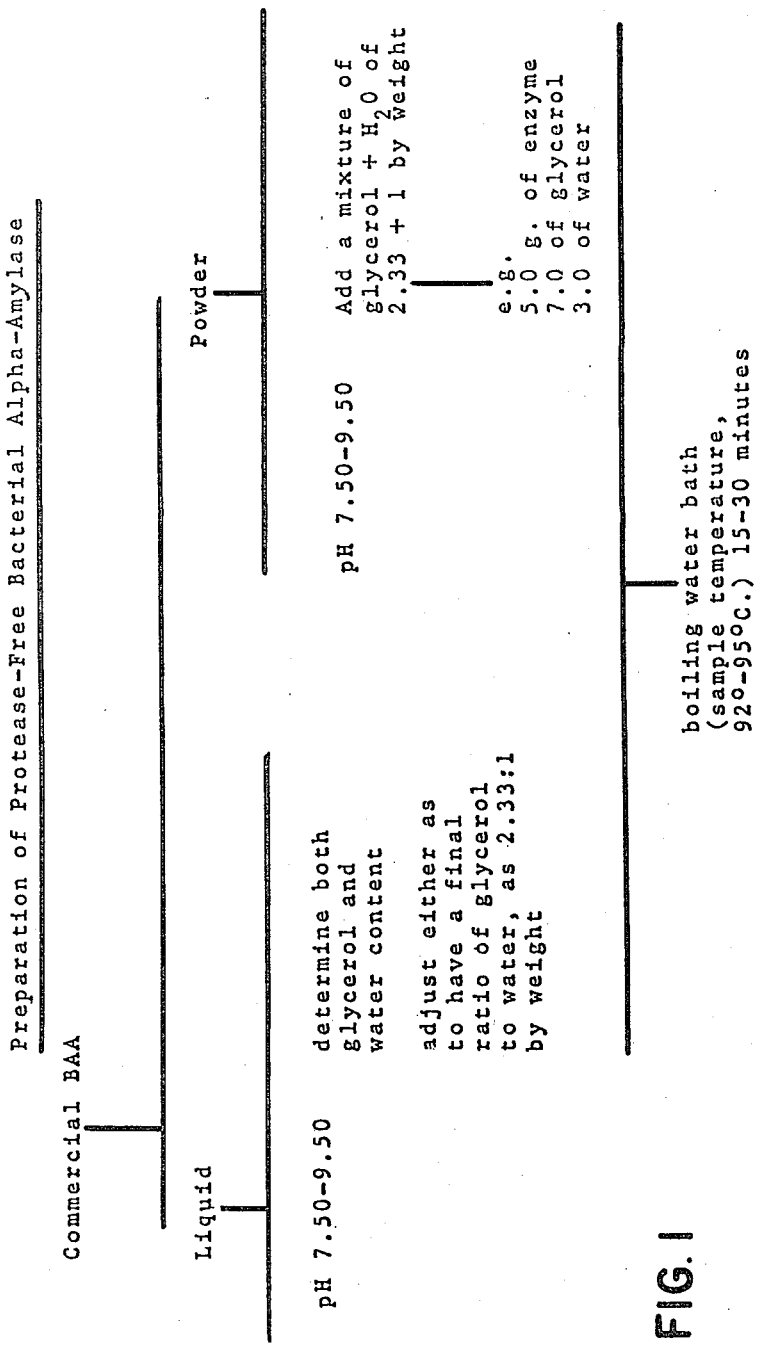
FIG. 1 is a process flow diagram for a commercial process for the manufacture of protease-free bacterial alpha-amylase.

In the following discussion, when the term "bread" is used, it is also implied that other bakery products such as rolls, muffins, biscuits, donuts, crackers or cake are also included. As used hereinafter, the term "alpha-amylase" except as indicated, is meant to include commercial preparations of heat stable bacterial alpha-amylase enzyme, obtained from *Bacillus subtilis*, and the term modified alpha-amylase to mean alpha-amylase preparations, which have been treated to inactivate the proteolytic enzyme activity contained in the original commercial preparations while stabilizing or retaining the alpha-amylase activity. The term "dough" is hereinafter used as a broad meaning and includes not only conventional bread doughs but also cake batters, cracker mixes and other uncooked bakers products. The term "flour" as hereinafter used is also used in a broad sense to include meal and other starchy ingredients of bread.

The bread staling processes can be divided into two parts: the staling of the crust and the staling of the crumb. The staling of the crust, which is relatively unimportant, changes the dry, crisp crust of fresh bread into a soft, leathery coating and is due mostly to transference of moisture from the center to the outside of the loaf. This staling is more noticeable in wrapped loaves. The staling or firming of the crumb which is the subject of this invention is of much more importance and is what is commonly recognized as staling. The texture of the crumb becomes harder, tougher and more crumbly and increasingly opaque as the bread stales.

Baking studies were conducted to determine the effect of commercial bacterial alpha-amylase on bread staling. Several enzyme levels were used. The effect of loaf quality when commercial bacterial alpha-amylase was added at the sponge stage, is indicated in Table I. According to the results obtained, the higher levels cause the loaf to collapse accompanied by a very sticky crumb structure, while the lower levels had little effect on bread softness. Depending on the level of the commercial enzyme used, the bread crumb was quite sticky, loaf volume was low and the bread grain was coarse. When 0.0003% enzyme was used, the bread had a normal appearance, very slightly sticky to the touch and no detectable reduction in bread firmness. It is apparent from these results that the commercial alpha-amylase cannot be used to prevent bread staling and enhance bread quality due to the destructive effect these preparations have on bread quality.

Since the architecture of the bread structure is dependent upon a protein-starch matrix, it was contemplated that the destructive effects obtained when using commercial alpha-amylase may be due to the combined action of proteolytic and amylolytic enzyme activity, which could destroy the bread structure. Samples of commercial alpha-amylase enzyme preparations were analyzed to determine the protease and alpha-amylase content of several commercial preparations.

Ten bacterial alpha-amylase preparations, which were obtained from five different suppliers were assayed for both the alpha-amylase and protease activity for the manufacture of a protease-free alpha-amylase for use in baking. The samples varied widely and activity is indicated in Table II. The ratio of alpha-amylase to protease varied from 1:0.04 to 1:2.60 (D.U.:HUT). Different enzyme potencies were noticed from lot to lot. Variability in enzyme potency among the commercial samples as well as existing variations from lot to lot, clearly demonstrates the necessity for bacterial alpha-amylase purification for consistent effects in bread products.

Modification of Commercial Alpha-Amylase

A process was developed for the inactivation of the proteolytic enzyme, while retaining the alpha-amylase activity. The method used involves heating a solution of the commercial alpha-amylase enzyme in a buffer solution, under control conditions of time, temperature, pH and specific ion concentrations.

A 0.5 M sodium acetate buffer was adjusted to various pH values with either sodium hydroxide or an acetic acid solution. 1.750 grams of the commercial bacterial alpha-amylase enzyme (Rhozyme H-39) was diluted to 100 ml. with water. 2 ml. of the enzyme solution was added to the sodium acetate buffer solutions in each of the predetermined pH values. The commercial amylase solutions, adjusted to the desired pH, were heated at 40°, 50°, 60° and 70° C. for exactly 30 minutes. The thermally treated enzyme solutions were cooled immediately to room temperature, then analyzed for residual protease enzyme activity using A.A.C.C. Method 22-62.

The effect of pH and temperature on the rate of protease enzyme inactivation is illustrated in Table III. The results obtained from this study indicate that the protease enzyme of a commercial bacterial alpha-amylase preparation is progressively susceptible to inactivation in the 40°-70° C. temperature range. The maximum protease inactivation is obtained at 70° C. The rate of inactivation is also influenced by the operating pH of the enzyme solution during the thermal treatment. The more favorable pH range for protease inactivation is below pH 7.00. Since the bacterial alpha-amylase enzymes are rapidly inactivated below pH 5.00, although exhibiting maximum activity at pH 6.10, it is believed that pH 6.00-6.50, and 70° C. would be the preferred conditions to use for the inactivation of bacterial protease and still retain alpha-amylase activity.

Ten milliliters of 0.05 M sodium acetate buffer solution were pipetted in a series of tubes. The buffer was adjusted to pH 6.50 with 2% acetic acid solution. 2 ml. of the commercial bacterial alpha-amylase was added to each tube then transferred to a water bath set at 70° C. Appropriate tubes were removed from the water bath after exactly 5, 10, 20 and 30 minutes of heating, then immediately cooled to room temperature. An enzyme sample was held at room temperature (no thermal treatment), to be used as a reference point (control).

Both treated and untreated enzyme solutions were assayed for protease activity and the results are indicated in Table IV. The bacterial protease enzymes, under given conditions, are nearly inactivated within 15 minutes at 70° C. Quantitative inactivation of all protease enzyme was obtained after heating the enzyme solution at 70° C. for 30 minutes.

The effects of concentration and ionic composition of different buffer solutions upon the degree of inactivation of protease enzyme, contained in commercial alpha-amylase are illustrated in Table V. 0.1 M, 0.5 M and 1.0 M sodium acetate buffer solutions were adjusted to pH 6.50. 10 ml. of each buffer were mixed with 2 ml. of enzyme (35 milligrams) then heated at 70° C. for 30 minutes. Sodium, potassium and calcium acetate solutions, (0.5 M) were adjusted to pH 6.50. 10 ml. of each buffer solution were mixed with 2 ml. of enzyme then heated to 70° C. for 30 minutes. Sodium and calcium chloride solutions (0.5 M) were adjusted to pH 6.50. 10 ml. of each salt solution were mixed with 2 ml. of enzyme then heated to 70° C. for 30 minutes. All the samples were cooled to room temperature then assayed for a protease activity.

The rate of inactivation of bacterial protease enzymes was inversely related to the concentration of the buffer solution containing the commercial enzyme. Bacterial protease was rapidly inactivated in water and in sodium acetate buffer concentrations from 0.1 M to 0.5 M. When using 1.0 M sodium acetate buffer, the bacterial protease enzymes were somewhat protected by the buffer during the thermal treatment. This shielding effect of bacterial protease by 1.0 M sodium acetate is illustrated in Table V where 41.3% residual protease activity was found under the stated conditions of thermal treatment. Therefore, higher buffer concentrations should be avoided for the inactivation of the bacterial protease contained in commercial bacterial alpha-amylase preparations. A dilute buffer concentration from 0 to 0.1 M sodium acetate which is capable of maintaining a constant pH 6.00-pH 6.50 during the thermal treatment at 70° C. is desired.

The buffer salt used to dissolve the commercial enzyme is important. After a thermal treatment of 30 minutes at 70° C., 55.2% and 97.1% residual protease activity remains when the commercial enzyme preparation is dissolved in potassium or calcium acetate buffer solutions, respectively. Of the various buffer salts studied, sodium acetate does not interfere with the thermal inactivation of the bacterial protease. Sodium acetate is contemplated as being a preferred buffer salt in the process for the modification of commercial alpha-amylase.

It was shown that the presence of the chloride ion has a debilitating effect on the protease enzymes. The presence of sodium chloride slightly enhances the rate of bacterial protease inactivation while less protease inactivation is obtained with calcium chloride. Residual protease activity was present after the thermal treatment when sodium chloride and calcium chloride are both added to a commercial enzyme solution, prior to heat treatment.

EXAMPLE I

Commercial bacterial alpha-amylase, Rhozyme H-39 was modified by the heat purification technique described above. 1.750 grams of the commercial bacterial alpha-amylase was diluted to 100 ml. of water. Two ml. of enzyme (35 milligrams) was mixed with 10 ml. of 0–0.1 M sodium acetate buffer solution adjusted to a pH of 6.00–6.20 using acetic acid. 0.5 M sodium chloride solution was added to the above mixture and heated at 70° C. for 30 minutes. The protease activity was reduced to a non detectable level.

Conditions for the inactivation of all protease activity and the commercial bacterial enzyme preparation is noted above. Studies are conducted to determine whether the alpha-amylase activity is also effected by these conditions. The results show that thermal treatment at 70° C. for 30 minutes reduces the activity of both the protease to 0 and the amylase activity to about 10% in the absence of sodium chloride. From Example I, the alpha-amylase activity is not effected by the thermal treatment when about 0.5 M sodium chloride is present in the enzyme solution. The presence of the sodium chloride during the thermal treatment has a stabilizing effect on the alpha-amylase activity and slightly enhances the heat inactivation of the protease enzyme. The stabilizing effect of sodium chloride on the alpha-amylase during heat inactivation of the protease is shown in Table VI.

Either 0.200 grams or 0.250 grams of the commercial bacterial alpha-amylase enzyme was dissolved in 50 ml. of 0.050 M sodium acetate buffer solution, pH 6.10, which also contains 0.1 M, 0.3 M, 0.5 M, 0.8 M, 1.0 M, or 1.5 M sodium chloride. These enzyme solutions (pH 6.0–6.2) were heated at 70° C. for 30 minutes, rapidly cooled to room temperature then diluted to 500 ml. with water. The residual alpha-amylase activity after thermal treatment was determined in each enzyme solution and indicated in Table VI. The maximum bacterial alpha-amylase activity stability was obtained when 0.5 M–0.1 M sodium chloride was added to the commercial enzyme solution prior to heating at 70° C. It is noted that the sodium chloride has a protective effect on the bacterial alpha-amylase activity during the thermal treatment.

The stabilizing effect of sodium chloride on the alpha-amylase activity was further demonstrated when a heated enzyme solution was stored at room temperature for 31 days without loss of alpha-amylase activity. 0.25 grams of the commercial activity alpha-amylase and 0.5 M sodium chloride was dissolved in 100 ml. of 0.1 M sodium acetate buffer solution (pH 7.00). The enzyme solution was heated at 70° C. for 30 minutes and then diluted with 500 ml. of water. 0.25 grams of the commercial bacterial alpha-amylase was also dissolved in 0.1 M sodium acetate solution, pH 6.20. This enzyme solution was not heated and does not contain any sodium chloride. Both samples were held at room temperature for 31 days. Aliquots of the two enzyme solutions were withdrawn periodically to assay the amylase activity.

The results indicate that when a dilute water solution of bacterial amylase (0.50%) (no sodium chloride added) is stored at room temperature, the amylase activity progressively decreases until no activity remains at the end of the 19th day, while a thermally treated enzyme solution, which contains 3% (0.5 M) sodium chloride, exhibits no major change in the bacterial alpha-amylase activity during a 31 day storage period. Dilute enzyme solutions can therefore be kept for a long period of time at room temperature without reduction in alpha-amylase activity by merely adding sodium chloride to the enzyme solutions.

EXAMPLE II

Commercial alpha-amylase from Rohm and Haas, Rhozyme H-39 was assayed for protease enzyme activity and alpha-amylase enzyme activity prior to heat treatment. The protease activity before treatment was measured at 7874 HUT/g. on an as is basis. The alpha-amylase activity before heat treatment was measured at 37,500 DU/g. on an as is basis. The sample of Rohm and Haas commercial alpha-amylase was prepared by first dissolving in 0.05 M sodium acetate (pH 6.00–6.20) and 0.8 M sodium chloride solution. The enzyme solution was heated at 70°–72° C. for 30 minutes, then cooled to room temperature. Under these conditions, a purified bacterial alpha-amylase was obtained which was virtually free of protease enzymes. The protease enzyme activity measured after heat treatment was 0 HUT/g. and the alpha-amylase enzyme activity after heat treatment was 37,500 DU/g on an as is basis.

EXAMPLE III

The experiment of Example II was repeated on a commercial bacterial alpha-amylase preparation obtained from Miles Laboratory, HT-1000 which had a measured protease enzyme activity of 11,854 HUT/g. Prior to heat treatment and an alpha-amylase enzyme activity of 24,000 DU/g. before heat treatment. After treating the commercial enzyme preparation under the conditions of Example II, the protease enzyme activity measured 0 HUT/g. and the alpha-amylase enzyme activity measured 24,000 DU/g. on an as is basis.

The result given in Examples II and III indicate that there was considerable variability in both the protease and the amylase activity in the commercial enzyme preparations. The alpha-amylase purification procedure noted above successively reduces the protease enzyme activity to a very low value while having no effect on the alpha-amylase activity.

EXAMPLE IV

Bacterial alpha-amylase purification was obtained by dissolving the commercial bacterial enzyme preparation in 0.05 M sodium acetate buffer (pH 6.10) and 0.8 M sodium chloride, and then heating at 70°–72° C. for 30 minutes. After the heat treatment the enzyme solution was cooled to ambient temperature. Under these conditions, the protease enzyme was inactivated while 100% alpha-amylase activity was retained. This procedure was successful for purification of a number of commercial enzyme preparations.

According to the literature, bacterial alpha-amylase necessitates the presence of calcium ions for thermostability. Additional levels of calcium ions were selected from compounds consisting of calcium sulphate, calcium chloride and calcium phosphate, monobasic. 0.50 g. of HT concentrate bacterial alpha-amylase from Miles Laboratory and 4.7 g. of sodium chloride were diluted to 100 ml. (pH 6.5). Each enzyme solution was prepared with 0.2% calcium sulphate, calcium chloride and calcium phosphate, heated at 75° C. for 30 minutes then assayed for amylase activity.

The comparative effect of the 0.2% solutions on the amylase activity is indicated in Table VII. Both calcium chloride and calcium phosphate enhance the heat inactivation of the amylase during the thermal treatment at 75° C. Based on these results calcium sulphate was selected for further investigations.

The effect of calcium sulphate on the amylase and protease activity at 75°, 80° and 97° C. were investigated. 0.500 g. of Miles Laboratory HT concentrate and 4.7 g. of sodium chloride were diluted to 100 ml. of water (pH 6.50). Each enzyme solution was prepared with and without calcium sulfate (0.0006 M). Because of the low solubility in water only 0.0006 M calcium sulphate was used in this investigation. The enzyme was heated for 30 minutes at respective temperatures and the pH of each enzyme solution was determined before and after the thermal treatment. The results of the investigation are shown in Table VIII.

When heating the commercial enzyme (pH 6.50) at 75°, 80° and 97° C. the amylase activity was progressively reduced. Greater activity was retained at 75° and 80° C. when calcium sulfate was added to the enzyme solutions. At 97° C. only 3% of the original alpha-amylase activity remained after the thermal treatment. 0.8 M sodium chloride at pH 6.50 preserved the activity to 70° C. while the presence of 0.0006 M calcium sulphate in combination with 0.8 M sodium chloride improves the thermal stability of the alpha-amylase up to 75° C. By contrast, treatment of the commercial enzyme for 30 minutes at 75° C. reduces the protease activity from 362,000 to 1228 HUT/g. No additional protease activity was obtained when the treatment was conducted at higher temperatures.

Since calcium sulphate improves the stability of the amylase at 75° C., experiments were conducted to determine the stability as a function of concentration. Table IX shows the results obtained from this experiment. Increased concentrations in calcium sulfate does not result in corresponding improvement of the enzyme stability of 75° C. Maximum stability is obtained when 0.0003 M to 0.00012 M calcium sulphate was used. Above 0.0012 M calcium sulphate exerts an inhibitory effect on the amylase activity. Therefore, 0.0006 M calcium sulphate appears to be a preferred concentration.

A process is contemplated for the adsorption of the purified bacterial alpha-amylase on wheat starch to preserve the stability of the alpha-amylase at 75° C. A study was conducted to determine the effect of calcium sulphate and wheat starch on the alpha-amylase activity during heating at 75° and 80° C. 0.500 g. of HT concentrate, 4.7 g. of sodium chloride, 0.0006 M calcium sulphate and 1.0, 3.0 and 5.0 g. of wheat starch were diluted to 100 ml. The enzyme solutions were heated at either 75° or 80° C. for 30 minutes as indicated in Table X.

Thermally treating the commercial enzyme with 0.8 M sodium chloride only, at 75° C. results in a deactivation of the alpha-amylase activity. Amylase stability was improved when 0.0006 M calcium sulphate was combined with 0.8 M sodium chloride. Maximum enzyme stability was obtained when a commercial enzyme was heated at 75° C. together with 0.8 M sodium chloride plus 0.0006 M calcium sulphate plus 1% wheat starch. At 80° C. the alpha-amylase activity was slightly reduced when treated in the presence of these 3 components. Increased wheat starch concentrations do not improve enzyme stability.

The time temperature relationship necessary for the heat inactivation of the protease enzyme of a commercial bacterial alpha-amylase was studied and its effect on the alpha-amylase activity. 1.500 g. of Miles HT concentrate, 14.1 g. of sodium chloride, 0.450 g. of calcium sulphate at pH 6.50 were diluted to 300 ml. of water. All ingredients without the enzyme were brought to 70° C., 75° C. and 80° C. respectively. The HT concentrate was added and mixed vigorously for several minutes. After every 10 minutes of heat treatment, a 20 ml. aliquot of the enzyme solution was withdrawn and rapidly cooled to ambient temperature. Samples were taken every 10 minutes for two hours then stored in the refrigerator until after assayed.

The results indicate that the alpha-amylase activity remains fairly constant for 70 minutes at 70° C. Slight reduction in activity is obtained after heat treating the enzyme for 80 to 120 minutes. At 75° C. the activity is constant for 30 minutes. While at 80° C., the alpha-amylase was 100% active during the first 10 minutes. Thereafter, the activity progressively decreased from 133333.2 DU/g. to 12000.0 DU/g. at the end of two hours. At 70° C. the protease enzyme was progressively inactivated during a two hour period. At 75° C. the protease was reduced to trace levels after 20 minutes. At 80° C. the activity was reduced to trace levels after 10 minutes. The most salient points from the experiment can be summarized as follows: The protease enzymes of a commercial amylase can be reduced to trace levels when using 0.5% enzyme concentrations which have been adjusted to pH 6.5 with 2% acetic acid, and heated at 75° C. for 15 to 30 minutes in the presence of 0.8 M sodium chloride, 0.0006 M calcium sulphate and 1 to 3% wheat starch. The degree of protease inactivation obtainable when using increasing concentrations of the commercial alpha-amylase is reported in Table XI. The commercial example had a pH of 8.45. Before usage, Maxamyl LX-6000 (Enzyme Development Corporation) was adjusted to pH 6.5 with acetic acid. The 0.500, 2.50, 5.00, 10.00, 15.00, 20.00, 25.00, and 35.00 grams of LX-6000 were diluted to 50 ml. Each enzyme solution contains 0.0006 M of calcium sulphate, 0.8 M of sodium chloride and 1 g. of wheat starch. After thorough mixing, the solutions were transferred to 200 ml. volumetric flasks. The enzyme solutions in volumetric flasks were heated to 75° C. and held at this temperature for 30 minutes. After heating, the samples were cooled to room temperature and assayed for amylase and protease activity.

From Table XI some differences in amylase activity were obtained. These differences may seem high in some cases; however, when the amylase values were averaged, the mean of the heated samples was not too different from the control (unheated). One can expect very little loss, if any, in amylase activity obtained when purifying from 1% to 70% of the commercial liquid amylase concentrate. The protease of the commercial amylase was progressively reduced from 2698 HUT/g. to 0, depending on the enzyme concentration used before the thermal treatment at 75° C. for 30 minutes. According to the amylase to protease ratio shown in the last column, up to 50% concentration of the enzyme can safely be purified for use in bread.

In summary, the developed method of purification involves the following conditions:

| | |
|---|---|
| 1. a. 0.8M NaCl | |
| b. 0.0006M CaSO$_4$ . 2H$_2$O | |
| c. 1–3% wheat starch | adjusted pH 6.50 |
| d. enzyme | |

2. Bring solution to 75° C. (without enzyme and starch).
3. At 75° C., add the enzyme and wheat starch.
4. Hold for 15 to 30 minutes, depending on the enzyme concentration used as well as the initial protease level in the commercial amylase.
5. Use the same procedure for all commercial preparations. Should the protease be still present after 30 minutes at 75° C., then increase the wheat starch and time at 75° C., while keeping the other conditions constant.

EXAMPLE V

A commercial enzyme concentration for use in the purification process was about 10% of the liquid concentrate. According to this example, Miles Laboratory, HT concentrate was used as a source of alpha-amylase. 60 DU/800 g. of flour of purified alpha-amylase have been used in the sponge dough process, and therefore 3405.0 DU are needed per 100 pounds of flour. Using a 10% commercial enzyme concentration in the purification step, the solution contains 900,000 DU per 100 grams of solution. A solution was prepared using 0.8 M sodium chloride plus 0.0006 M calcium sulphate in 100 ml. of water and heated to 75° C. 10 grams of commercial enzyme (as is) and 1.0–3.0 g. of wheat starch were added to the solution and adjusted to a final pH of 6.50. The solution was heated at 75° C. for 15 to 30 minutes and then cooled to room temperature. 100 grams of the purified enzyme solution equals approximately 900,000 DU. After purification the purified enzyme was adsorbed on an inert starch carrier. Approximately 200 grams of wheat starch were added to the purified enzyme solution to make about a 50% slurry and mixed thoroughly. 0.200 g. of starch contains about 900 DU of amylase. The 50% slurry was sequentially diluted by the addition of dry starch. The solution was diluted to 100 times or to 20 kilograms of starch. The resulting 1 gram of starch yielded about 45 DU of amylase.

Bread Baking Studies Plus Surfactant

Bread baking studies were conducted using both commercial alpha-amylase enzyme preparations and purified alpha-amylase to determine their effects on bread quality and rate of bread firming using the Instron Universal tester. The sponge dough formula in Table XII was used to measure the effect of the alpha-amylase activity in bread. The test breads were made into 18¾ ounce loaves, placed in standard 10⅛ inch × 4¾ inch metal baking pans, proofed to ¾ inch above top of pan at 110° F., then baked in 415° F. oven for 20 minutes. The breads were allowed to cool for 60 minutes, then each loaf was individually packaged in moistureproof polyethylene bags.

Loaves were sliced after 1, 3 and 6 days of storage at room temperature. Slices were selected at specific points of the loaf for measurement of bread firmness with the Instron Universal tester.

The conditions used to measure bread firmness with the Instron Universal tester (model 1102) were as follows:
Full scale load: 1 lb.
Plunger: 1⅜ inches in diameter
Compression: 0.20 inches per minute
Bread sample thickness: 1 inch Six readings were made on each loaf of bread. Samples were selected from a symmetric design. Bread firmness is directly related to the height of the peak, (maximum force), which is translated to percent of full scale. The reported values were converted from pounds to grams full scale. A high numerical value represents a bread of high firmness.

The effect of varying levels of the purified alpha-amylase upon the rate of bread firming, based on Instron firmness values obtained on bread after 1, 3 and 6 days storage are shown in Table XIII. It is apparent from the data as shown in Table XIII that the addition of 0–72.2 DU of the purified alpha-amylase/800 g. of flour (14% MB) has little effect on either the bread softness or rate of bread firming. The commercial alpha-amylase for the foregoing experiments was purified by taking 0.200 g. of the commercial preparation (Miles HT-1000), mixing with 4.7 g. of sodium chloride (0.8 M) and 1 ml. of 0.5 M sodium acetate transferring to a 500 ml. volumetric flask. A mixture was dissolved in 100 ml. of water with a final pH of 6.2–6.50. The flask containing the enzyme solution was transferred to a water bath which was preset at 70°–72° C. and kept at this temperature for 30 minutes, then cooled to room temperature. The enzyme solution was diluted to 500 ml. with water.

Baking studies were conducted to establish the level of purified bacterial alpha-amylase in combination with 0.5% calcium stearate required to obtain the desired anti-staling effect in bread. The effect of different levels of purified alpha-amylase when used in combination with 0.5% calcium stearate (based on flour) is clearly demonstrated in Table XIV. The results given in Table XIV clearly demonstrate that reduction of bread firming was progressively obtained when 0.5% calcium stearate was used in combination with increasing levels of purified bacterial alpha-amylase.

EXAMPLE VI

Breads were baked using 300 DU of the commercial alpha-amylase, Rhozyme H-39, and 0.5% calcium stearate per 800 g. of flour (14% MB), and the same enzyme source, same level of alpha-amylase (300 DU) after the Rhozyme H-39 was modified by heat treatment to inactivate the proteolytic enzymes. The results obtained using commercial vs. purified alpha-amylase show that the bread made using commercial alpha-amylase has a low loaf volume, open cell structure and a sticky, gummy bread crumb while the bread using purified alpha-amylase had a satisfactory loaf volume and cell structure and the bread crumb was not as gummy as the bread made using the commercial alpha-amylase.

The changing rate of bread firming during a 1 to 6 day storage period using different levels of purified alpha-amylase in combination with 0.5% calcium stearate is shown in Table XV. The data in Table XV show that the rate of bread firming was remarkably decreased when using a combination of 54–72 DU of enzyme and 0.5% calcium stearate. When using this combination, bread has as fresh a crumb texture at the end of 6 days as bread made with 0.5% surfactant after 3 days. The combination of the purified bacterial alpha-amylase and calcium stearate is an effective method for control of bread firming. The surfactant system alone promotes greater initial bread softness, however, the rate of staling was the same as bread made without surfactants.

The method described above, using combination of purified heat stable bacterial alpha-amylase enzyme plus calcium stearate as a surfactant is the first effective method to be developed for the control of staling in bread and other baked products. The inhibition of bread firming obtained, using a combination of purified alpha-amylase enzyme plus 0.5% calcium stearate was not due to improved moisture retention in the bread crumb since there is virtually no change in the moisture content over a 6 day storage period as shown in Table XVI.

The effect of purified alpha-amylase concentration when used in combination with 0.5% calcium stearate on loaf quality is illustrated in Table XVII. In the evaluation of the bread quality, crumb color and grain score were taken into account. The addition of 0.5% calcium stearate in combination with increasing levels of the purified amylase produces a bread having a very tender crumb texture. The degree of tenderness is directly related to the level of enzyme added to the dough. The presence of 72 DU of amylase produces a crumb having a very slightly gummy character in the mouth; however, this is not objectionable and was found to be subjective. The addition of 90 to 150 DU of the purfied amylase produces a slightly softer sponge than normal. Dough handling properties were similar to the control sample. General bread properties were similar to the control except that the grain was slightly more open when using the 90–150 DU level of enzymes. Lack of resiliency and increasing crumb tackiness was directly related to the level of enzyme added to the dough. It was clear that staling was nearly arrested during a six day storage period when employing 130–150 DU of purified bacterial alpha-amylase in combination with 0.5% calcium stearate. It was unnecessary to use higher levels of enzyme since no further benefit can be obtained from such practice. Since the highest levels of enzymes ever needed to inhibit staling is 150 DU, it is pointed out that bread properties and sliceability are acceptable up to 300 DU.

The data presented thus far show that 0–72 DU of enzyme without calcium stearate has little effect on the rate of staling. The combination of 18–72 DU of enzyme plus 0.5% calcium stearate progressively retard bread firming. The desired range is found to be between 45–72 DU of enzyme. When operating this range bread freshness obtained at the end of 6 days was comparable to the bread made using only surfactant at the end of the third day. Complete inhibition of bread firming was nearly achieved when using 130–150 DU of purified enzyme in combination with 0.5% calcium stearate. However, the crumb texture was slightly tacky and gummy due to the presence of above normal levels of dextrins in the bread. There was sufficient evidence to show that the combined effect of calcium stearate in the purified alpha-amylase in bread was synergistic and not cumulative.

Baking studies indicate that the degree of anti-firming in bread was directly related to the presence of 0.5% calcium stearate and increasing levels of the purified amylase. The following experiments were undertaken to determine whether increased anti-firming effect in bread can be obtained by varying the concentration of calcium stearate in combination with a fixed level of the purified amylase. Sunny Kansas flour was used in the baking studies in combination with Miles HT-1000 bacterial alpha-amylase and calcium stearate obtained from MCB.

Table XVIII shows the effect of various levels of the purified amylase and calcium stearate on the rate of bread firming and bread quality. The addition of the purified amylase to bread exerts little, if any, anti-firming action when calcium stearate was absent from the mixture. Bread firmness can be restrained by manipulation of the concentration of the purified amylase and the calcium stearate. The same degree of anti-firming activity can be obtained by employing a higher concentration of calcium stearate in combination with a low level of enzyme activity or vice-versa. This approach allows great flexibility in the control of bread firming. Except for very subtle differences, which only an experienced baker can detect, bread quality in all of the above examples is normal.

Since a desired anti-firming effect in bread can also be obtained by manipulating the level of calcium stearate, in combination with a fixed level of purified amylase, additional studies are conducted with 0.5–2.0% calcium stearate in 54 DU of amylase. The results of this study are summarized in Table XIX.

During the first three days of the storage, no major differences in anti-firming effect were obtained by varying the calcium stearate concentration from 0.5% to 2.0%. The anti-firming action of higher concentrations of calcium stearate become much more evident at the end of the sixth day of storage. The level of action was directly related to the concentration of calcium stearate used in combination with 54 DU of purified alpha-amylase.

A comparison of bread firmness data shows that similar anti-staling effects were achieved when using either 0.5% calcium stearate plus 90–110 DU or 1% calcium stearate plus 54 DU of purified alpha-amylase. Little additional effect was obtained when increasing the concentration of calcium stearate from 1% to 2% as illustrated in Table XX. Bread made with 0.5% calcium stearate plus 90–150 DU of purified amylase has an increasingly gummy crumb texture at higher enzyme levels, while no differences in either proof time or loaf volume were observed in these breads. Proof time was normal whether bread was made with either 0.5% or 2% calcium stearate, combined with 54 DU of enzyme. Loaf volume was also normal using 1% calcium stearate; however, when bread is made with 2% stearate, the volume decreases by 15 cubic inches. Since firmness measurements were influenced by the specific loaf volume, it was suspected that bread made with 2% calcium stearate would have been less firm if it had a normal volume. The evaluation of the internal loaf quality indicates to be normal with no evidence of gumminess. The most salient difference between these two approaches to the inhibition of staling was a bread made with 54 DU of enzyme combined with 0.5 to 1% calcium stearate has a much more desirable crumb character. While the mechanism was not clear, it was contemplated that sufficient starch depolymerization was obtained with low levels of the purified amylase. As a result the dextrins produced by the enzyme do not contribute to bread firming and crumb tackiness because they probably form insoluble complexes with increasing concentrations of calcium stearate in bread.

In summary, baking studies were made with 45-63 DU of alpha-amylase and 0, 0.25 and 0.50% calcium stearate. Data shows the synergistic action of the amylase surfactant softener system on the rate of staling. At constant enzyme activity, the antistaling action was directly related to the increasing concentration of the calcium stearate added to the dough. Consequently, a similar degree of anti-firming activity was obtained by adding a high concentration of calcium stearate in combination with a low level of enzyme or vice-versa. Using this approach one can exercise great control over bread firmness. Additional data show that anti-firming effects in bread were obtained by using either of these two systems:

1. 0.5% calcium stearate plus 90-100 DU of purified alpha-amylase.
2. 1% calcium stearate plus 54 DU of purified alpha-amylase.

The second system is preferred because it also produces a normal crumb texture without indication of gumminess.

Commercial surfactants permitted by the FDA were studied with and without 54 DU of purified bacterial alpha-amylase to determine whether they act as antifirming agents. Various degrees of anti-firmness were obtained when surfactants and amylase are concurrently added to the dough. The following surfactants were studied:

1. Sodium stearoyl-2-lactylate (SSL), Lab. No. 3697 Steorolac S, item 444 (Paniplus Co.).
2. Calcium stearoyl-2-lactylate (CSL), Lab. No. 5855 Steorolac C, item 450 (Paniplus Co.).
3. Soft Touch having the following composition:

|  | % |
| --- | --- |
| SSL | 5.33 |
| Polysorbate-60 (P-60) | 11.00 |
| 90% Distilled Monoglycerides | 14.67 |
| Propionic Acid (99%) | .30 |
| Phosphoric Acid (85%) | .17 |
| Water | 68.53 |

4. Succinylated Monoglycerides (SMG), Lab. No. 2841 powder form, obtained from Eastman Kodak (DPI).
5. Ethoxylated Monoglycerides (EMG), no Lab. No., received from Paniplus Co.
6. Glycerol monostearate-90 (GMS-90), Lab. No. 2390-2, obtained from Breddo Products.
7. Polysorbate-60 (P-60), Lab. No. 822, received from ICI (Atlas Chemical Co.).
8. Oleic acid, OX 165, CB 554 practical, received from MCB.
9. Palmitic acid, Lot 6894 organic reagent, obtained from Mallinckrodt.
10. Stearic acid, SX 995, P 2733 practical, obtained from MCB.
11. Calcium stearate, SX 960, P 888, obtained from MCB.

The bacterial alpha-amylase enzyme used was from Miles Laboratories HT-1000. The surfactants were used on the same solid basis (0.5% of flour solids). Purified bacterial alpha-amylase levels used in all baking tests were 54 DU, a fresh solution being prepared before each baking test. Because of the limited number of doughs that can be handled in the baking tests, the surfactants were divided into the following groups:

|  | Group I |
| --- | --- |
| 1. | Control - no enzyme, no surfactant |
| 2. | Enzyme only |
| 3. | SSL |
| 4. | CSL |
| 5. | Soft Touch |
|  | Group II |
| 1. | Control - no enzyme, no surfactant |
| 2. | Enzyme only |
| 3. | Calcium stearate |
| 4. | SMG |
| 5. | EMG |
|  | Group III |
| 1. | Control - no enzyme or surfactant |
| 2. | Enzyme only |
| 3. | GMS-90 |
| 4. | P-60 |
| 5. | Mixture of oleic and palmitic and stearic (1 + .6 + .3/w) |

The anti-firmness effect of some commercial surfactants in bread are illustrated in Table XXI.

The addition of 54 DU of purified amylase to bread has virtually no effect on staling. The rate of firming was comparable to bread made with neither amylase nor surfactant. When 0.5% SSL, CSL and Soft Touch (solids basis) were added to dough, various bread softening effects were obtained. The crumb softening effect followed this order: SSL>CSL>Soft Touch. Inhibition of staling was obtained when 54 DU of the purified amylase was used in combination with the commercial surfactants. The order of effectiveness when the surfactant was used with the enzyme was: SSL>CSL>Soft Touch.

Results obtained from the second group of surfactants are shown in Table XXII.

As reported in Table XXI, bread made with the enzyme alone was as firm as the control, during six days storage. Bread was rendered softer when either calcium stearate or SMG was added to dough. Calcium stearate exerts a greater bread softening effect than SMG. EMG exhibits no effect on softness, in fact the obtained bread was as firm as the control. In Group II, the softening effect follows this pattern: calcium stearate>SMG>EMG.

Firming was drastically reduced when calcium stearate was used in combination with the purified amylase. The combined addition of the amylase and either SMG or EMG to bread had very little effect on the rate of firming. In Group II, only calcium stearate plus 54 DU of bacterial amylase changes the rate of staling.

Baking results obtained from the third group of commercial surfactants appear in Table XXIII.

Results obtained from Group III commercial surfactants followed the same pattern as those described in Group I and Group II. The addition of 0.5% GMS-90 (solids basis) to dough exerts the greatest crumb softening effect in bread than either polysorbate-60 (P-60) or the free fatty acids. During the first 3 days of storage, P-60 had no effect on crumb softness. At the end of 6 days softness was slightly lower than the control. Free fatty acids hydrate do not work as well as GMS-90 when added at the sponge stage. These results confirm our previous findings that the free fatty acids are most functional as bread softeners when added at the dough stage.

A combination of surfactant and purified amylase in dough inhibits bread firming during a 6-day storage period. In terms of functionality, the following pattern was obtained: GMS-90>FFA>P-60. A combination of 0.5% P-60 plus 54 DU of purified amylase has little effect on the rate of bread firming. Summarizing the results described in Tables I, II, III, the most functional surfactant plus enzyme combinations were: SSL, CSL, GMS-90 and calcium stearate and 54 DU of purified amylase.

Table XXIV shows the rate of change in bread firming during 6 days storage when using commercial surfactants in combination with 54 DU of amylase.

The rate of firming was greatly reduced over a six-day storage period when bread was made with either SSL, or Ca Stearate, or GMS-90 and 54 DU of purified bacterial alpha-amylase. P-60 and EMG were found to be the least effective. Soft Touch does not work as well as SSL or GMS-90 on the same solids basis because it contains P-60, which was found to be ineffective as a crumb softener.

In bread making, surfactants perform either or both of two important functions. They may serve as crumb softeners if their action is primarily on the starch fraction of flour, or dough strengtheners if they interact predominately with the gluten proteins. Using these specific definitions, we can classify the commercial surfactants permitted in bread as described in Table XXV.

In summary data shows that the enzyme alone causes little changes in staling. Surfactants alone increase bread softness. An anti-firming effect after 6 days of storage was obtained when the purified amylase was used in combination with various surfactants. According to rank of effectiveness, SSL, calcium stearate and GMS-90 exert the greatest anti-staling action in bread with an increase in Instron firmness value per day of 27.4 (control) 11.0(SSL), 12.0(calcium stearate) and 12.13(GMS-90). SSL and GMS-90 are as effective as calcium stearate when added in combination with the enzyme. The dough strentheners, EMG and P-60, plus the enzyme exert very little anti-staling action in bread. The data from the baking experiments show that the rate of firming was greatly reduced when the purified bacterial amylase was added to dough along with commercial surfactants which act primarily on the starch fraction, crumb softners.

Dry Preparation

The next concern of this invention is with the development of a dry purified alpha-amylase preparation, loosely adsorbed on an inert carrier for easy introduction into the dough mixture. In utilizing the purified alpha-amylase, it may be desirable to provide a more concentrated solution of the purified alpha-amylase enzyme. One technique of concentration is the precipitation of the bacterial alpha-amylase with organic solvents. The effect of various organic solvents on the precipitation of bacterial alpha-amylase from dilute aqueous solutions is illustrated in Table XXVI. The results indicate that no loss in amylase activity is obtained when a dilute enzyme solution (0.5%) is treated with any of the organic solvents noted. The solvent precipitation method when using 1:4 ratio is a very effective way to concentrate the bacterial alpha-amylase from dilute aqueous solutions.

Further studies indicate that the bacterial alpha-amylase was almost quantitatively precipitated from dilute aqueous solutions when an acetone ratio of at least 1:1 by volume was used as indicated in Table XXVII.

After concentration of the bacterial amylase, it is desirable to loosely adsorb it on a suitable inert carrier, such as starch. Granular wheat starch is contemplated as being useful for this purpose. A commercial bacterial alpha-amylase was purified according to the method described above. The purified amylase solution (200 ml=4,800 DU) is stirred with 50 g of prime wheat starch; 800 ml. of acetone is added and stirred for 10 minutes, then centrifuged at 800–1000 RPM for 5 minutes. The starch was dried at room temperature for 1 hour, then vacuum dried at 22°–23° C. overnight. This starch containing the amylase was pulverized. The results indicate that 0.625 g of starch carries 60 DU of amylase. Accordingly, 0.625 g of starch were used per 800 g of flour in bread baking tests. The antifirming effect of the bacterial alpha-amylase on starch during a 6 day storage period is indicated in Table XXVIII. The anti-firming effect of the alpha-amylase on the starch carrier was comparable to the enzyme solution.

The addition of bacterial alpha-amylase to the chlorinated tap water resulted in an enzyme inactivation. However, when the enzyme was added to the dry bread formula components first, followed by the addition of the water, the enzyme remained active. In reviewing the bread formula ingredient list, it seemed reasonable to assume that calcium sulfate, wheat starch and wheat flour might offer good enzyme stabilizing properties. The stabilizing effect of these three materials is shown in Table XXIX, wheat flour was the only formula ingredient to exhibit any enzyme stabilizing effect in tap water.

Since flour stabilizes the bacterial amylase activity in tap water, it was determined that the stability is not affected by the pH of flour suspension. Flour stabilized the bacterial amylase activity in the pH range 3.40–6.10. In the pH range of breadmaking flour not only stabilized the enzyme but also enhanced its activity. Therefore, flour exerts its effect both as a stabilizer and as an activator. At pH 5.20, Table XXX illustrates the minimum flour concentration per 500 ml. of chlorinated tap water necessary to stabilize the bacterial amylase.

When using 0.2% flour in tap water, 6.4% of the relative activity was lost. Maximum enzyme stability was obtained when using 0.6%. Flour concentration above 0.6%, i.e. 1.0–4%, progressively activated the bacterial amylase, under the same experimental conditions. Maximum activation appeared to occur with 2.0–5% flour concentration. Since all previous experiments were conducted with enriched patent flour, it is quite possible that the enrichment components might be related to the enzyme stability.

The vitamins alone did not exert a stabilizing effect on the bacterial amylase. However, ferrous sulfate had a positive effect on the stability. Since chlorine is primarily involved in the inactivation of the enzyme in tap water, ferrous sulfate counteracts this effect through a redox reaction, whereby the ferrous ion is oxidized to the ferric state by chlorine. For this reason, the ferrous sulfate must always be added to the tap water first, followed by the addition of the enzyme. Reversing the sequence of ferrous sulfate and the enzyme leads to the inactivation of the latter. Table XXXI illustrates the effect of pH on the ability of ferrous sulfate to stabilize the bacterial amylase in tap water.

Ferrous sulfate exerted a stabilization effect on the enzyme above pH 6.50. At pH 5.80, ca. 85% of the original activity was lost. It is apparent that in the pH range of breadmaking (pH 5.00–5.50), ferrous sulfate will offer little help in the stabilization of the bacterial amylase in tap water. However, ferrous sulfate in combination with the flour could exercise a greater stabilizing effect. Assuming a favorable pH environment prevails, Table XXXII illustrates the minimum ferrous sulfate concentration needed, per 100 ml. of tap water, for enzyme stability.

At pH 8.60, maximum bacterial amylase stability was attained when premixing at least 0.3 mg. of ferrous sulfate with 100 ml. of tap water (8° C.).

Data presented in Table XXIX showed that the bacterial alpha-amylase activity was well preserved in the presence of flour. Since the flour used in all the experiments was enriched, it was shown that ferrous sulfate was also effective in stabilizing the enzyme activity. Whether the ferrous sulfate in the flour solubles was primarily responsible for the enzyme stability wasn't too clear. To answer this question, both an enriched and unenriched flour were compared in Table XXXIII. Both enriched and unenriched flour were equally effective. From this experiment, it is deduced that the enzyme stabilizing agent(s) is inherently associated with the flour, and is independent of the added ferrous sulfate.

In summary the addition of bacterial alpha-amylase to chlorinated tap water resulted in an enzyme inactivation. In order to prevent such inactivation, calcium sulfate, wheat starch and wheat flour were explored as potential stabilizing agents. Flour was the only one to exhibit this effect. Moreover, 81% of the stabilizing action resided in the water soluble fraction of flour. Furthermore, flour not only stabilized the enzyme in the pH range 3.50–6.10; but also exerted its effect as an activator. A minimum of 0.6% flour concentration (w/v) in tap water was found to be necessary for the enzyme stability.

Since the flour used in this study was enriched, and the stabilizing agent(s) was found to be water soluble, experiments were run to determine the effect of the flour enrichment components on the enzyme stability. Only ferrous sulfate had a positive effect. In the absence of flour, the protective action of ferrous sulfate diminished greatly in the pH range of breadmaking. Whether enriched or unenriched, the stabilizing effect of flour was the same. This observation leads one to conclude that the stabilizing agent(s) is inherently associated with the flour, and not necessarily resulting from the ferrous sulfate enrichment. Data obtained from this study illustrated 3 possible ways to counteract the ill effects of chlorinated tap water by: (1) preheating the water to between 50°–100° C. for 5–15 minutes to removed chlorine, (2) adding at least 0.3 mg of ferrous sulfate per 100 ml., above ph 6.50, (3) adding at least 0.6 g. of flour per 100 ml. The adsorption of the bacterial amylase on a flour carrier seems to be the best approach.

The process previously described sufficiently reduced the protease concentration of the commercial bacterial alpha-amylase to trace levels for use in breadmaking. In summary, the procedure consisted of a thermal treatment of 75° C. of a 10% commercial enzyme solution, at pH 6.20–6.50 and containing 0.8 M NaCl, 0.0006 M $CaSO_4 \cdot 2H_2O$ and 1.0–3.0% wheat starch, the duration of the treatment was 15–30 minutes, depending on the commercial enzyme concentration and the potency of the protease. These conditions developed in the laboratory were easily translated to a pilot scale, so that a commercial process was developed for both: 1. protease-free bacterial alpha-amylase, 2. protease-free amylase in wheat starch tablets for use in breadmaking.

Research conducted demonstrated very clearly that the bacterial alpha-amylase is immediately and irreversibly inactivated upon contact with tap water. In bakeries, the normal practice is to add all additives, in the form of tablets to tap water. Additional experiments showed that the enzyme deactivating effect of tap water was primarily attributed to chlorine. Wheat flour, not wheat starch, acted as an excellent enzyme stabilizer in tap water. Since the chlorine concentration of tap water is variable, i.e., depending on the season and geographic location of the bakery, this research was conducted to develop a commercial process for the enzyme treatment and its adsorption on wheat flour. Techniques were explored to develop another commercial process for the manufacture of a protease-free bacterial alpha-amylase (PBAA) on a flour carrier, for use in breadmaking. 1. A liquid enzyme concentrate (Maxamyl) was acetone precipitated onto wheat starch to prepare a dry enzyme concentrate, which was (or could be) dry blended with wheat flour to obtain the desired enzyme concentration. 2. A liquid enzyme concentrate (Maxamyl) was sprayed into and blended with dry wheat flour. 3. Dry enzyme tablets were prepared using a liquid enzyme concentrate adsorbed onto wheat flour, which was then blended with other dry ingredients and pressed into tablets. The concurrent spraying and blending techniques (2.) was the preferred route. The final product obtained by either method (1.) or method (2.) was found to be acceptably uniform. It is suspected. suspected that product uniformity could be further improved by extending the mixing time. The spraying and blending technique experimented with is greatly dependent upon the use of a concentrated enzyme solution, such as 90,000–100,000 DU/ml.

PBAA ON WHEAT FLOUR

Several approaches were tried for the development of a commercial process for the manufacture of a protease-free bacterial alpha-amylase (PBAA) on a flour carrier. The first technique involved the preparation of a concentrated enzyme-wheat starch product, as to have a potency of 18,000 to 24,000 DU per gram of starch, using an acetone precipitation method. Liquid bacterial alpha-amylase (PBAA) Mexamyl) 20–25 g. as is, was slowly added to 100 g. of wheat starch suspended in 500 ml. of acetone. After mixing, the entire suspension was filtered through a Buckner funnel. The starch-enzyme product was air dried until acetone could no longer be detected. The dried product was pulverized with a mortar and pestle, then passed through a 200 mesh sieve. The obtained concentrated product ($1.8-2.3 \times 10^4$ DU of alpha-amylase per gram of wheat starch) was added on top of 100 lbs. of wheat flour in the Littleford Mixer, model FM 130D. The obtained concentration product (100 g.) was then dry blended with 100 lbs. of wheat flour. Dry blending a concentrated PBAA on either starch or flour with wheat flour to any enzyme concentration desired appears quite feasible.

The second and preferred approach involved spraying the PBAA solution and concurrent blending with wheat flour. When using this technique, dilute aqueous enzyme solutions should be avoided, otherwise the water content of the final product would be too high and an additional step would be needed to dry the product to a safe moisture level (the drying may deactivate the enzyme). The reservoir of the spraying device was filled with 50 g. of the liquid enzyme ($4.5 \times 10^6$ DU) and sprayed on 100 lbs. of wheat flour for 15 minutes.

Spraying 50 g of PBAA on 100 lbs. of wheat flour does not change appreciably the final moisture of the product. In this experiment, spraying and blending was conducted continuously for 15 minutes. A product of greater uniformity could be obtained by spraying for 15 minutes, then interrupt the spraying and continue blending for another 5-15 minutes. Undoubtedly, this technique would be the preferred route in developing a commercial process for the manufacture of PBAA on a flour carrier.

Enzyme tablet-making was the third approach explored. The following attempts were made with:

1. 100% wheat flour (as is) (ADM, Red July 17, 1978)
2. Acetone dehydrated and defatted wheat flour
3. 80% flour+20% Avicel (FMC Corporation)
4. 70% flour+10% Avicel+20% dicalcium phosphate
5. 50% flour+50% cerelose (glucose monohydrate)

Although the above combinations worked well in making the tablets, tablet disintegration in water and other physical characteristics were poor. Flour proteins offered the greatest obstacle. A combination of flour and cerelose showed great promise. After several experiments, the following composition produced tablets having typically desirable properties:

| Tablet Composition | % of Total Composition* |
|---|---|
| PBAA adsorbed on Wheat Flour | 8.33 |
| Wheat Flour | 44.84 |
| Cerelose 2001 | 44.83 |
| Syloid 266 | 1.00 |
| Magnesium Stearate | 1.00 |

The highest concentration of flour that could be used in table-making was 50% of the total weight. If one were to use tablets instead of bulk flour as a way of introducing PBAA in breadmaking, the tablet component PBAA on flour could be adjusted to any desirable enzyme potency. Because of the necessary presence of flour when PBAA is added to tap water, a safe approach would be to use tablets having an activity level of 300-500 DU (6 g. tablet) as to use 6-10 tablets per 100 lbs. of bread flour. Since the chlorine concentration in tap water varies with the season, as well as the geography, it seems that this approach could offer some definite disadvantages. PBAA on bulk flour is a more attractive and sounder approach, because it would be added to the other dry formula ingredients and not to tap water, as is generally done. The concurrent spraying and blending technique described above is the simplest and preferred way to manufacture the protease-free bacterial alpha-amylase (PBAA) on a wheat flour carrier.

PREFERRED PURIFICATION METHOD FOR BAA

Preliminary experiments gave positive indications that a protease-free BAA could be obtained by simply heating the commercial liquid enzyme (Maxamyl) in a boiling water bath for 30 minutes. Consequently, extensive experiments were conducted to develop the optimum working conditions. The obtained results showed that the pH (7.50-9.00) and a glycerol to water ratio (6.0-1.0:1/W), with a preferred ratio of 2.33:1/W, before the thermal treatment, were the two most important factors for maximum amylase stabilization at boiling temperatures.

Depending upon the original enzyme concentration, under these conditions analyses indicated the protease was inactivated after 15 minutes. The working conditions developed for the liquid enzyme were found to be equally applicable to a powder enzyme obtained from two different manufactures. Breads made with PBAA prepared by the prior method at 75° C. and the present method (92°-95° C.) were found to be comparable in anti-firming effect and crumb characteristics.

Experiments conducted gave positive indications that a protease-free BAA could be obtained by simply heating the commercial liquid enzyme in a boiling water bath for 30 minutes. When a test tube containing liquid enzyme was placed in a boiling water bath, the maximum internal temperature recorded has been in the range of 92°-95° C. Results showed that a low pH of the liquid enzyme sample was in part responsible for the inactivation of the BAA at 92°-95° C. Since the pH of the environment had a pronounced effect on the enzyme, an experiment was conducted to determine the effect of the pH on the enzyme activity.

When the commercial liquid enzyme was heated in the boiling water bath for 30 minutes, the bacterial alpha-amylase was rapidly inactivated below pH 6.00.

Since one of the major differences between the different liquid enzyme samples was the ratio of glycerol to water, an extensive experiment was conducted to determine the effect of both the glycerol and water concentration of the liquid phase on the BAA activity. After heating for 30 minutes at 92°-95° C., maximum BAA activity was maintained when the water concentration, making up the liquid phase, was in the 15-42% range. The amylase was rapidly inactivated above 42% water. The preferred level is 30%. The enzyme exhibited greater resistance to inactivation in more concentrated glycerol solutions, than in water. Although, in absolute glycerol ca 40% of the original activity was lost. Using a liquid enzyme having an optimum ratio of glycerol to water, the degree of BAA stability in a boiling water bath, as a function of time was determined. The commercial liquid enzyme exhibited remarkable amylase stability. After 4 hours at boiling temperatures only 30% of the original activity was lost. This loss of activity is probably attributed to a lowering of the pH from 8.30 to 6.20. Under the same heating conditions, the addition of either flour or flour plus sodium chloride had a deteriorating effect on the BAA stability. Results obtained from previous experiments strongly suggest that the pH and the ratio of glycerol to water are the two most important factors necessary for maximum preservation of the BAA at boiling temperatures. The effect of these same conditions on the protease activity as a function of time was determined.

When testing the liquid enzyme no protease activity was found after 5 minutes at 92°-95° C. The powder enzyme was reduced from 28,000 to 130 HUT/g. protease activity at the end of 15 minutes. Samples containing greater protease concentrations than these may require longer than 15 minutes in boiling water. Since the pH and the glycerol to water ratio were found to be critical to amylase stabilization and protease inactivation of a commercial liquid BAA, an experiment was conducted to determine whether these conditions could also be applied to commercial powder enzymes. (Table XXXIV).

Figure 2:
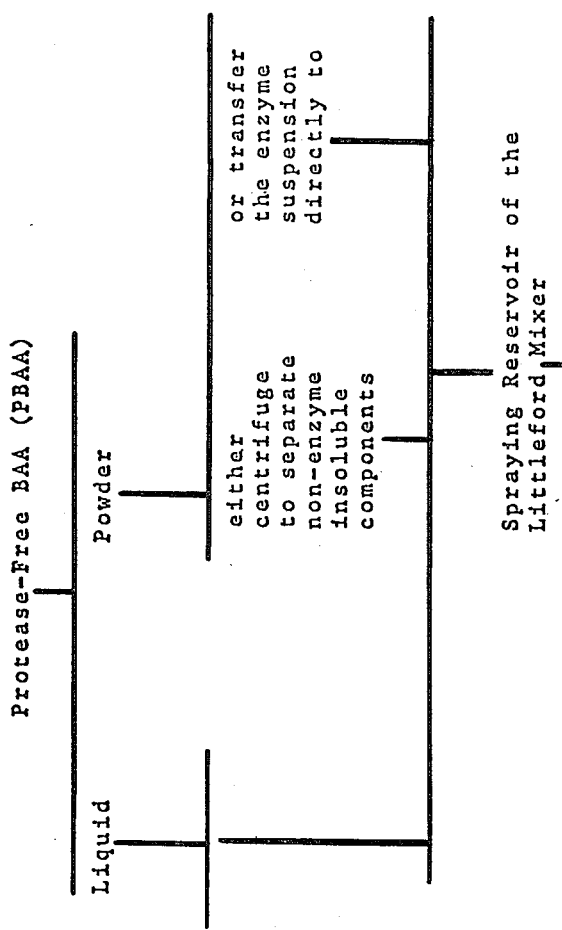
FIG. 2 is a process flow diagram for the introduction of purified alpha-amylase on wheat flour for use in bread making.

Results in Table XXXIV demonstrate that the pH and glycerol to water ratio developed for the commercial liquid enzyme worked equally well on commercial powder enzymes. As long as these conditions are carefully observed, this approach makes the protease inactivation step of a commercial process extremely simple. The protease of the commercial Maxamyl liquid enzyme was inactivated by two methods, at 75° C. and at 92°–95° C. The obtained protease-free BAA was then added to a bread dough to compare both their anti-firming effect and bread crumb characteristics. (Table XXXV). A process flow diagram for the commercial process for the manufacture of protease-free bacterial alpha-amylase is illustrated in FIG. 1 and its introduction on wheat flour for use in bread making in FIG. 2.

The values appearing in Table XXXV demonstrate that the anti-firming effect was similar, whether the protease was inactivated at either 75° C. or at 92°–95° C. Moreover, BAA treated at 92°–95° C. produced a bread having better crumb quality.

ALCOHOL FRACTIONATION

In previous baking experiments, the observation was made that PBAA prepared from different commercial manufactures did not produce bread of the same internal quality. Consequently, the PBAA was fractionated with methanol plus 5.0% NaCl solutions to isolate enzyme fractions which produce a bread improvement effect while maintaining the desired anti-firmness activity. PBAA enzyme fractions were precipitated with 54.5, 58.3, 61.5, 64.3 and 66.7% methanol, then studied in breadmaking. Maximum bread quality was obtained with the (61.5%) fraction, closely followed by the (58.3%) fraction.

Since the (61.5%) fraction makes up only 18–20% of the original enzyme activity, a baking experiment was conducted to determine whether co-precipitated (61.5%) and (58.3%) fractions (48–50% enzyme activity) exert as good a bread improvement as the separate fractions. Bread quality evaluation of the co-precipitated enzyme fractions was similar to the (61.5%) fraction alone. Additional baking tests showed that the bread quality was virtually alike whether methanol or ethanol was employed in PBAA fractionations.

One of the primary objectives of the present research was to see whether PBAA could be "cleaned up" in a way as to produce the same quality bread regardless of the enzyme manufacturer. Maxamyl LX-6000 and HT-Concentrate were selected because in previous experiments they produced the most diverse effects on bread quality. Breads of equal quality were obtained when the PBAA, representative of both sources, was precipitated with (66.7%) methanol. A commercial process for the purification and adsorption of the PBAA on a flour carrier is described.

In past baking experiments, the Bread Laboratory observed that the internal bread quality was not always the same when thermally treated bacterial alpha-amylase (PBAA) from different suppliers was added to a dough system. Since the employed PBAA samples used were free of any proteolytic activity, it was deducted that the variation in bread quality could have been due to non-amylase components, which apparently are typically present in commercial enzyme preparations. With these thoughts in mind, the present research had a two-fold purpose:

A. To determine if the functional properties of the PBAA could be improved.

B. To determine whether a PBAA product could be prepared that would give uniformly good bread quality and anti-firming activity, regardless of the commercial enzyme manufacturer of the *Bacillus subtilis* bacterial alpha-amylase enzyme.

Most of the research on the enzyme fractionation was conducted using Maxamyl LX-6000, Lab No. 312 (1977), received from Enzyme Development Corporation. Where indicated, the other enzyme source used was HT-Concentrate, Lab No. 197 (1977), received from Miles Laboratories. In all baking experiments, bread was made by the sponge-dough process, without making any alterations in the baking procedure. Except where indicated, the enzyme used in the described experiments was Maxamyl LX-6000, which was prepared protease-free at 92°–95° C. (PBAA). It is also contemplated that the commercial enzyme could be prepared protease-free at 70°–75° C. (PBAA) according to this invention.

In order of facilitating the precipitation of the enzyme, the water phase of the methanol solution was replaced by a 5% NaCl solution.

Figure 3:
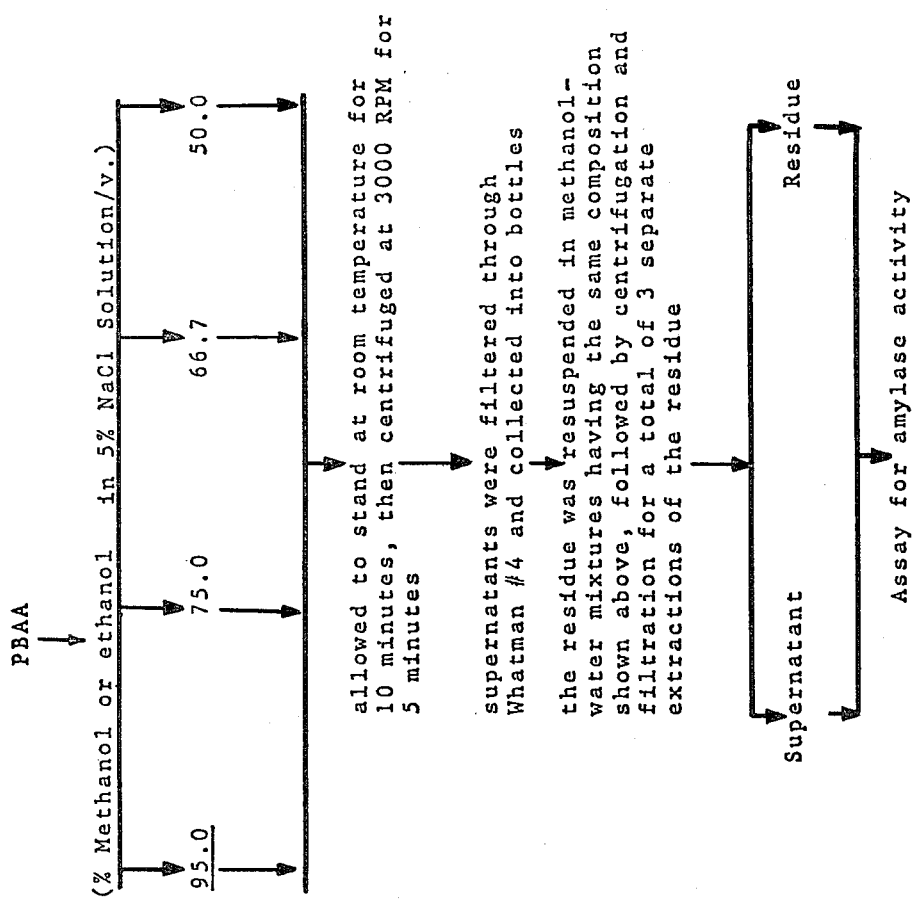
FIG. 3 is a process flow diagram for adding several levels of absolute methanol or ethanol to an enzyme-solution.

The PBAA was dissolved in 5% aqueous NaCl. Five grams (5 g.) of wheat flour were mixed with the enzyme solution to promote greater stabilization (flour addition was omitted from subsequent experiments because the enzyme was found to be equally active in the absence of flour). Several levels of absolute methanol were added to the enzyme-flour mixtures according to the process illustrated in FIG. 3.

Fractionation of PBAA using varying ratios of methanol to 5% NaCl solution was conducted. Ten grams (10.00 g) of PBAA was dissolved first in 50 ml of 5% NaCl solution, followed by 50 ml of absolute methanol and thorough mixing. After standing for 10 minutes, the methanolic enzyme solution was centrifuged at 3000 RPM for 5 minutes.

All enzyme fractionations were conducted at room temperature. In the early stages of the enzyme fractionation work, the precipitate was always dissolved in 5% NaCl solution (pH 6.50), then stored in the refrigerator until needed. Under these conditions, the enzyme stability was found to diminish with time. To improve the stability, in subsequent fractionations the precipitate was dissolved in minimum amount of water (ca. 5 ml), then adsorbed on wheat starch (ca. 50 g.), using the acetone technique previously described.

Figure 4:
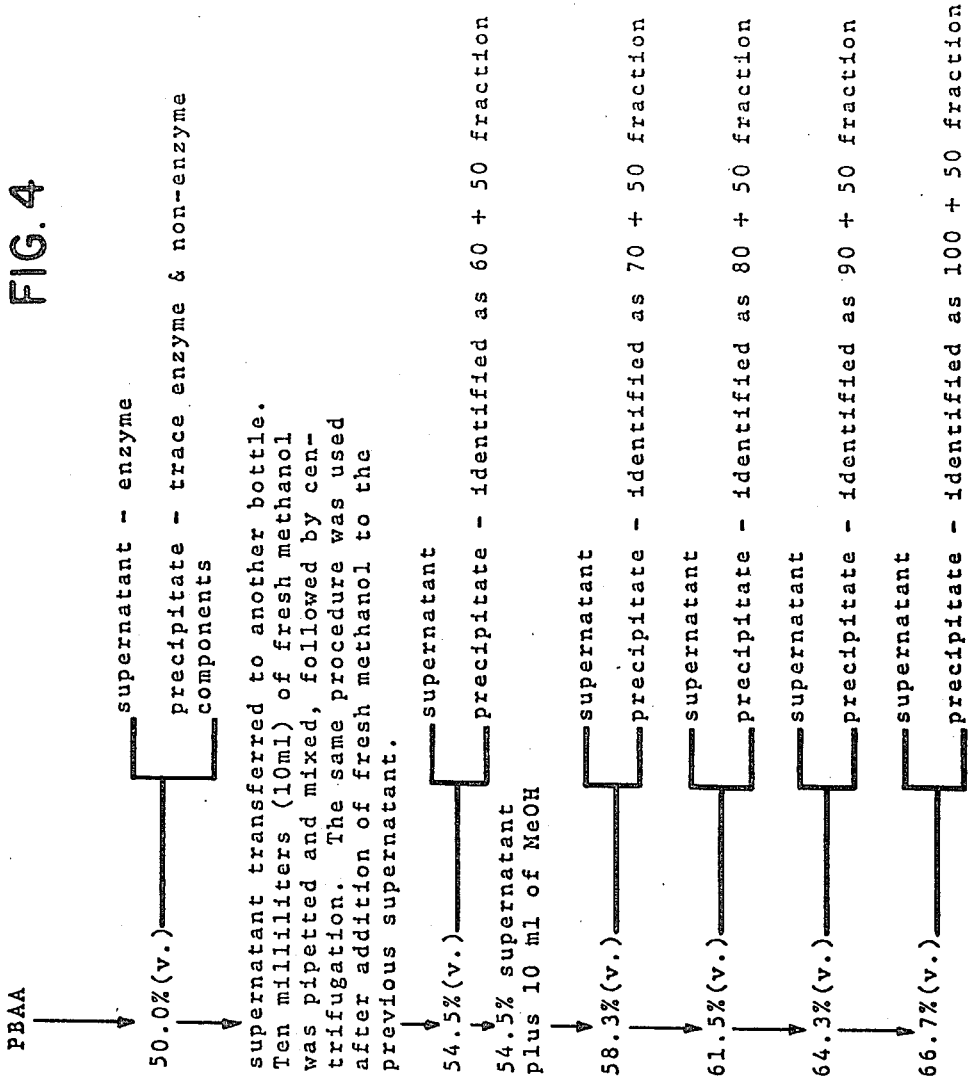
FIG. 4 is a process flow for obtaining various fractions of purified alpha-amylase by alcohol fractionation.

In certain baking experiments, group enzyme fractions were studied. For example, the following designation: 60→90/50 (54.5%→64.3%) means that the PBAA is first dissolved in 50 ml of 5% NaCl solution, followed by 50 ml of methanol, then centrifuged at 3000 RPM for 5 minutes. The supernatant obtained [50%(v.) methanol solubles] contains 90–100% of the starting enzyme activity. The 50% methanol soluble material was mixed thoroughly with an additional 40 ml of absolute methanol to increase the volume ratio of methanol to 90 hence 60→90/50(v.) (54.5%→64.3%). Using this procedure, the 60→90/50 (54.5%→64.3%) group fraction collectively represents the (60+50 or 54.5%), (70+50 or 58.3%), (80+50 or 61.5%) and (90+50 or 64.3%) fractions, as described previously and illustrated in FIG. 4.

Figure 5:
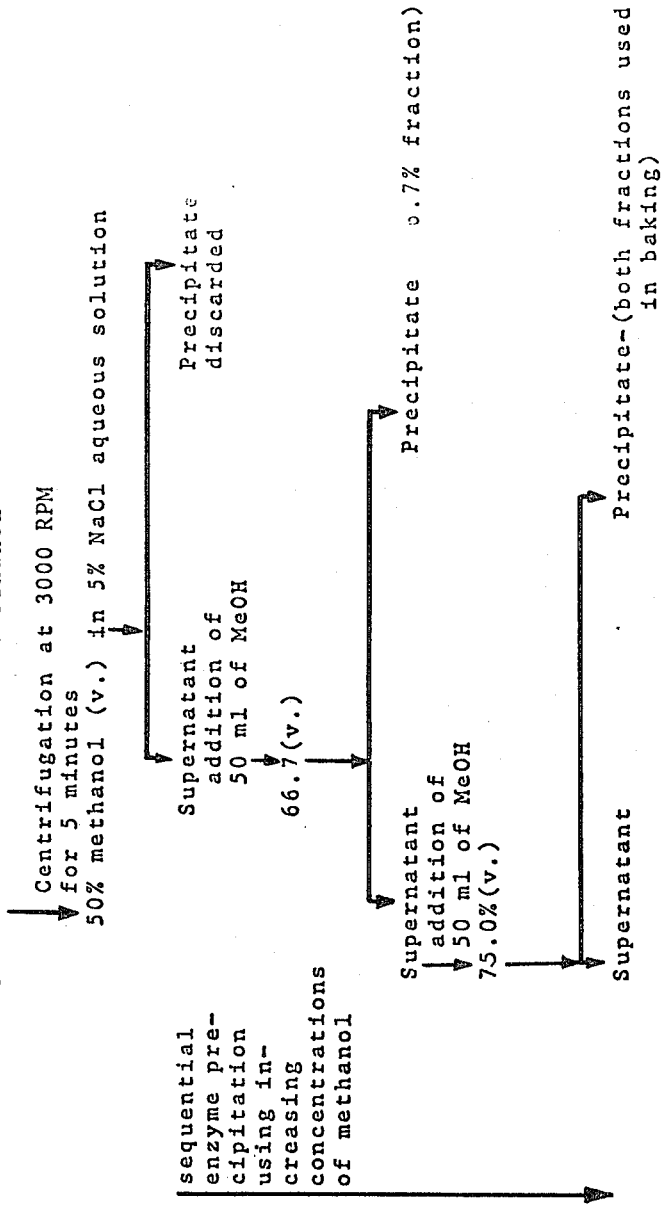
FIG. 5 is a process flow diagram as a preliminary approach of purified bacterial alpha-amylase Maxamyl and of HT-concentrate.

Comparative effect of PBAA from Maxamyl and HT-Concentrate on bread quality after methanol fractionation of the PBAA was studied. Maxamyl and HT-Concentrate were selected for this comparative test because they gave the most diverse results in bread quality in previously reported baking experiments. As a preliminary approach in "cleaning up" the PBAA of Maxamyl and of HT-Concentrate, the path was followed as illustrated in FIG. 5.

The following Maxamyl and HT-Concentrate fractions were tested in baking:

a. 50.0%(v.) methanol solubles—All of the enzyme activity plus color and other non-enzyme components.

b. 54.5–66.7%(v.) precipitate—85–90% of the original activity. Most color components absent.

c. 68.8–75.0%(v.) precipitate—10–12% of the original activity. Some color components absent.

d. 68.8–75%(v.) supernatant 1–2% of the original activity. Color components present plus other non-enzyme material.

The above baking experiment was conducted with 150 DU of amylase, in order to place a heavy stress on the bread test system.

Classical enzyme fractionations use either organic water miscible solvents or inorganic salts, such as ammonium sulfate [$(NH_4)_2SO_4$]. The salts are very effective precipitants, however, on a commercial scale, after recovering the desired enzyme fraction, the salts must be removed by the slow process of dialysis or by reverse osmosis. Water miscible solvents, such as the short chain alcohols, are preferred because they are easily removed.

Preliminary fractionating experiments were conducted with Maxamyl, using methanol —5% NaCl solutions of varying ratios. Table XXXVI describes the results obtained from this experiment.

The above experiment was conducted for several reasons:

a. Determine the feasibility of PBAA fractionation b. See whether the amylase activity is affected by the fractionating conditions c. Approximate the limits of total enzyme solubility and total enzyme precipitation in aqueous methanol.

Results obtained from this preliminary fractionating experiment clearly illustrated that:

a. NaCl was important in accelerating the enzyme precipitation at room temperature;

b. Color compounds and other non-amylase components ("inactive") could be separated from the alpha-amylase.

In fact, the extend of color removal was inversely related to the methanolic concentration. Observations made in this experiment have led to the process as illustrated in FIG. 6 as a way to "clean up" the Maxamyl PBAA.

As a result of the preliminary fractionation experiment described in Table XXXVI, another experiment was conducted for the purpose of fractionating a major enzyme fraction into subfractions to isolate those fractions which exert an improvement effect on bread quality. (Table XXXVII). The subfractions were obtained as precipitates by varying the ratio of methanol to 5% NaCl solution, then studied in baking.

The addition of various enzyme fractions (75 DU) isolated from the Maxamyl PBAA, to the sponge side resulted in bread having different crumb characteristics. Bread quality seemed to follow a parabolic function. Maximum quality was obtained with the (61.5%) fraction, closely followed by (58.3% fraction. Bread made with the (54.5%) and 64.3) and (66.7%) fractions produced bread of lower quality. These breads had a gummier and coarser grain, with inferior overall crumb characteristics, than either the (50.0%) fraction or the unfractionated PBAA. By contrast, the (61.5%) fraction was very close to the control (no PBAA). The Instron bread firmness values obtained at the end of the sixth day of storage were practically alike. The results suggest the anti-staling action of the various fractions (75 DU) in bread was nearly the same, only the crumb quality differed.

Relative quantities of the enzyme fractions recovered by the alcohol fractionation technique appear in Table XXXVIII. The solubility of Maxamyl PBAA in alcohol—sodium chloride aqueous mixtures is largely dependent upon the alcohol concentration. Results shown in Table XXXVIII clearly demonstrate that PBAA was nearly 100% soluble in solutions having 1:1 (v:v) (MeOH:$H_2O$). However, as the alcohol concentration increased from 50.0 to 66.7% (v.) enzyme fractions, possibly of different molecular weights, progressively precipitated out of solution.

The (58.3%/v.) fraction was the largest fraction with 37.3% of the original enzyme activity, followed by the (61.5%) fraction with 18.1%. Data provided in Table XXXVIII further show that ca. 90% of the original enzyme was precipitated out of solution when the alcohol concentration was increased from 50.0 to 66.7%.

The (66.7%) solubles consisted mainly of non-enzyme colored compounds, as well as ca. 10% of the original PBAA activity. The approach followed in Table XXXVIII provides us with a simple PBAA "clean up" procedure. A PBAA solution is first dissolved in 50%, then centrifuged. Non-enzyme material is sedimented under these conditions. The alcohol concentration is then raised to (66.7%), and again centrifuged to remove non-enzyme colored compounds. The PBAA precipitated with the alcohol —5% NaCl mixture (66.7%) is dissolved in water-glycerol mixtures then absorbed on wheat flour.

Although the Instron bread firmness data in Table XXXVII gave no indications of any reduction in antistaling activity, it is quite possible that the isolated PBAA enzyme fractions could exhibit different action patterns on gelatinized wheat starch. To see whether this was true, the isolated enzyme fractions were incubated with gelatinized soluble starch (Lintner) at 30° C. for 24 hours. The resulting malto-oligosaccharides were then analyzed by chromatography (TLC).

When a bacterial alpha-amylase is incubated with gelatinized starch and amylolysis is allowed to take place for long periods of time, the final product is primarily composed of glucose, maltose, maltotriose, maltotetrose, maltopentose and maltohexose. It was shown that the alcoholic fractionation of PBAA exerted no major modifications on the action patterns of the bacterial amylase on the starch. Additional experiments further demonstrated that the thermostability of the amylase present in the enzyme fractions was nearly the same.

Relative quantities of PBAA precipitable by various ratios of methanol —5% NaCl aqueous mixtures were summarized in Table XXXVIII. The effect of various enzyme fractions (precipitates) in baking has also been treated in Table XXXVII. The 61.5%(v.) fraction exhibited good bread improving properties, closely followed by the 58.3%(v.) fraction. Since the 61.5% fraction makes up only 18–20% of the original PBAA activity, a baking experiment was conducted to determine whether co-precipitated (61.5%) and 58.3) fractions exert as good an improving effect as the single fractions. Maxamyl PBAA was first dissolved in 54.5%(v.), after centrifuging out the resulting precipitate, the methanol concentration of the supernatant was increased to 61.5%. The obtained 58.3%→61.5%(v.) precipitate (ca. 50% of the original activity) was added in baking to compare its bread quality to the controls (no PBAA).

Breads were evaluated after the sixth day of storage at room temperature. As expected, bread made with the PBAA was always softer and slightly gummier (but acceptable) than the control bread made without the enzyme. The addition of 58.3–61.5%(v.) fraction to the sponge improved the grain and crumb quality of the bread (mean of six doughs or 12 loaves of bread, baked on two different days).

Although such organic solvents as methanol or acetone are normally used to precipitate enzymes from aqueous solutions, the question has been brought up whether replacing methanol with ethanol affects the concentration and type of precipitate obtained when using methanol. In this experiment, absolute ethanol was used in the enzyme fractionation. The 58.3–61.5%(v.) fraction was prepared in the same manner both with methanol and ethanol. After dissolution of the precipitates, 75 DU of amylase were added to the sponge.

When unfractionated PBAA (protease inactivation at 92°–92° C.) was added to the sponge, the resulting bread was slightly inferior in quality than the control (no PBAA). Breads made with the methanol and ethanol precipitates were comparable in quality to the control and in the case of grain, the alcohol precipitated enzyme addition produced a slightly better grain. No distinguishable differences in bread quality were observed between the ethanol and methanol breads. A separate experiment showed that the relative amount of PBAA precipitated by either methanol or ethanol as a function of alcohol concentration was nearly equal.

Figure 7:
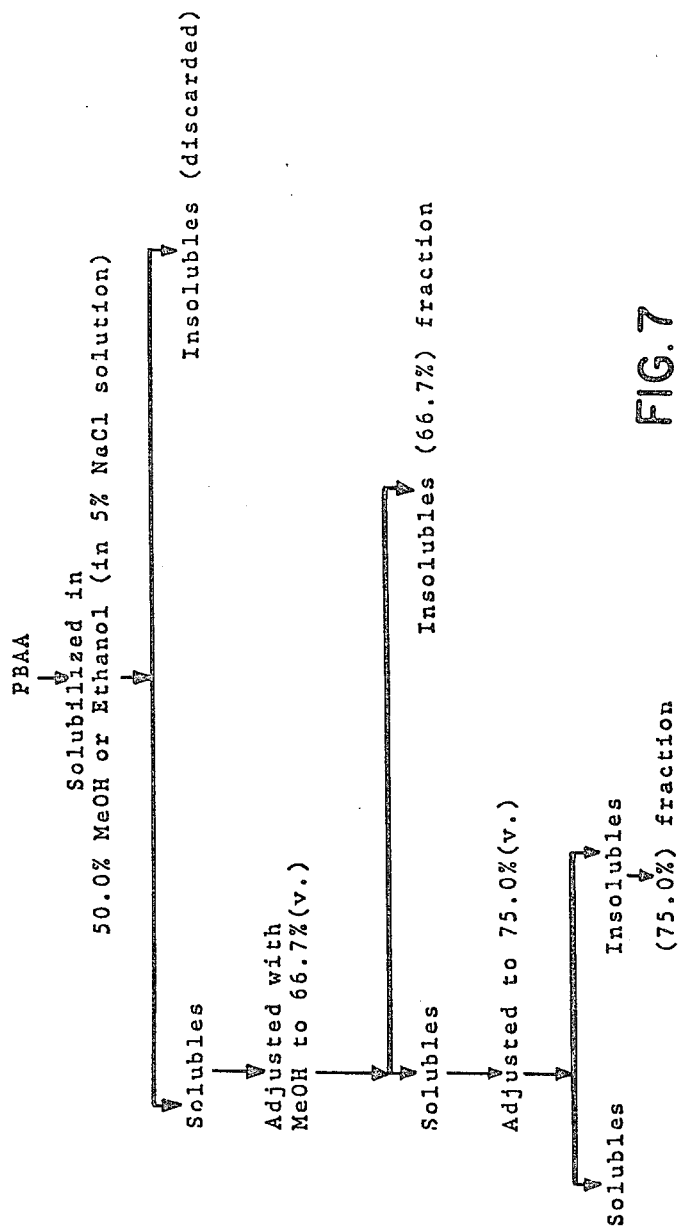

The previous baking experiments when involving the addition of PBAA from various commercial enzyme sources to a dough system, the observation was made in the Bread Laboratory that the resulting breads did not exhibit similar loaf quality characteristics. One of the primary objectives of the present research was to see whether the PBAA could be "cleaned up" in such a way as to produce the same quality bread, regardless of commercial enzyme source (manufacturer). Maxamyl and HT-concentrate PBAA were selected in this experiment, because in previous tests they produced the most diverse effects on bread quality. The PBAA "clean up" procedure used in this experiment is illustrated in FIG. 7.

Both the Maxamyl and HT-concentrate enzyme fractions exerted different effects on bread quality. The (50.0% solubles) and (66.7%) fraction improved the bread quality over the unfractionated PBAA, the 75.0% precipitate and the (75.0%)solubles. The (75.0%) solubles had a deteriorating effect on the crumb particularly with the HT-concentrate PBAA. Bread with best overall crumb quality was obtained with the enzyme precipitated with 50.0–66.7% methanol(v.). It was evident that the bread quality was greatly equalized when using the 66.7%(v.) fraction isolated from both Maxamyl and HT-concentrate.

Protease-free Maxamyl PBAA was fractionated with methanol plus 5% NaCl mixtures to isolate the PBAA fractions which possess the desired anti-firming activity when used in the Enzyme-Surfactant system, while improving the crumb quality. Both methanol and ethanol work equally well; therefore, either alcohol can be used to fractionate PBAA. Research described in this report was conducted using Maxamyl LX-6000 liquid enzyme (treated at 92°–95° C. for 30 minutes to render it protease-free (PBAA). Fractionation studies using Miles' HT-concentrate show the fractionation scheme developed for Maxamyl LX-6000 can be used equally well with other commercial bacterial alpha-amylase enzymes.

Although the anti-firming effect was the same whether the intact or fractionated PBAA was added to dough, the bread quality was improved when the commercial bacterial alpha-amylase (Maxamyl) was subjected to increasing degrees of purification:

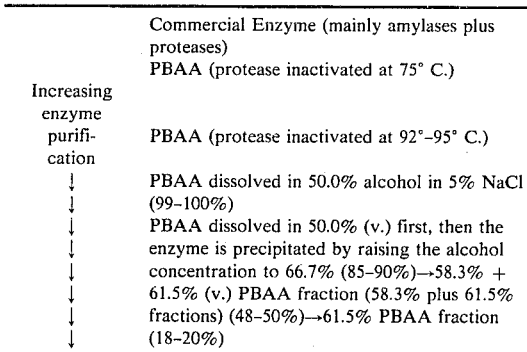

A commercial process for the purification and adsorption of the PBAA on a flour carrier is described in FIG. 8.

BREAD BAKING

A fresh sample of the commercial bacterial alpha-amylase was employed in all experiments. The commercial enzyme (BAA) was modified into PBAA, by heating at 75° C. for 30 minutes and as described previously. Bread baking experiments were conducted with and without 75 and 150 DU of amylase, in combination with 1% Panatex plus 0.3% SSL (all on flour basis), as surfactants. The above materials were added at the sponge stage.

The results presented indicate that the rate of firming occurred at a slower rate when the bread contained either BAA or PBAA. Furthermore, the bread made with the modified enzyme (PBAA) was evaluated as being superior in quality to bread made with the unmodified (BAA).

This study summarized the laboratory baking techniques, and testing procedures used to establish the effects of modified commercial bacterial alpha amylase enzymes, on standard enriched white bread.

The object was to prepare samples of white bread, using selected variables of commercial bacterial alpha amylase enzymes, modified commercial bacterial alpha amylase enzymes and enzyme free controls to determine the effect on shelf life and bread quality.

A standard laboratory test bake method was adopted for use in all bakes, with the only variables being (a) enzyme level, (b) type of enzyme (commercial or modified commercial) and (c) dough mixing time. The formula for the sponge and dough were as follows:

| STANDARD BREAD TEST FORMULA FOR ENZYME SOFTNESS BAKE FORMULA | |
|---|---|
| | Grams/Dough |
| Sponge Ingredients | |
| Flour, enriched (on 14% MB.) | 470 |
| Yeast | 20 |
| Yeast Food - (1) | 4 |
| Panatex - (2) | 8 |
| Sodium Stearoyl-2-Lactylate (3) | 2.4 |
| Water* | 302 |
| Flour + Enzyme Blend | 50 |
| Lard | 24 |
| Dough Ingredients | |
| Flour, enriched (14% M.B.) | 280 |
| Salt | 18 |
| Corn Sugar | 80 |
| Extram "C" (4) | 16 |
| Improved Paniplus (5) | 2.4 |
| Calcium Sulfate | 3.4 |
| Water* | 202 |

*Water adjusted to bring flour tp 14% moisture basis.
(1) Arkady Yeast Food - Standard Brands Co.
(2) Paniplus Co. - 22% alpha monoglyceride 68% water
(3) Patco - a dough strengthener
(4) Paniplus Co. - Milk replacement (80% soy flour 20% whey)
(5) Paniplus Co. - Blend containing raw soy flour and calcium peroxide.

PROCEDURE

A description of the unmodified and modified commercial amylases, and the corresponding usage levels, evaluated is presented in Table XL. It should be noted that the commercial unmodified amylase contains (1) more protease and (2) both the unmodified and modified enzymes were incorporated into flour at two activity levels. The low level may be regarded as typical of the usage level expected when producing bread under normal processing conditions. The higher level would rarely, if ever, be encountered in making bread. The enzymes were evaluated at the higher level mainly to accentuate the difference between the modified and unmodified enzymes.

The effect of enzyme modification on the crumb texture were the average firmness values, softness and gumminess obtained after two and six days of storage are as follows:

1. The control loaves firmness, softness and gumminess values differ significantly from the values obtained on the loaves prepared with the unmodified and modified enzymes. The control loaves are firmer, and not as soft and gummy as the loaves prepared with the modified and unmodified enzymes. This observation shows that both the modified and unmodified enzymes affect the crumb texture.

2. The loaves prepared with the unmodified and modified enzymes showed the greatest differences at the higher enzyme level after six days of storage. At this time the loaves prepared with the modified enzymes were significantly less gummy, firmer, and not as soft as the loaves prepared with the unmodified enzymes. This observation suggests that the undesirable characteristics (gumminess) of bread may be alleviated by modifying the enzymes before they are incorporated into the bread formulation.

3. After each storage period at 75 DU, the modified enzyme loaves were not as firm as the unmodified enzyme loaves. At 150 DU, the modified enzyme loaves were more firm, and not as gummy, as the unmodified enzyme loaves. This observation suggests that the commercial enzyme's undersirable effect on bread quality increases more rapidly with increasing concentration when the enzyme is not modified.

The effect of enzyme modification on the crumb appearance were the average grain and crumb character scores obtained on loaves after two and six days of storage are as follows:

1. The crumb character and grain is significantly effected by the addition of the modified and unmodified enzymes. The grain and crumb scores of the control loaves and the enzyme loaves are significantly different in seven of the eight comparisons.

2. The greatest differences in the crumb and grain scores observed between the loaves made with modified and unmodified enzymes occurred in the 150 DU loaves stored for six days. The loaves prepared with modified enzymes received significantly higher grain and crumb scores than the loaves prepared with the unmodified enzymes. This observation suggests that if enzymes are added to extend the shelf life, bread having a better crumb and grain will be produced when modified enzymes are used.

SUMMARY OF THE PREFERRED EMBODIMENT

Commercially available bacterial alpha-amylase obtained from extracts of *Bacillus subtilis* or *Bacillus sterothermophilis* in the form of a liquid or a powder can be purified, i.e. inactivation of the protease enzyme, by heating in a boiling water bath. A sample of liquid commercial alpha-amylase is adjusted to a pH from 7.50–9.50. The sample is assayed for its glycerol to water ratio and adjusted to a ratio of from 6.0–0.1:1/W with a preferred ratio of 2.33.1/W. The sample is placed in a boiling water bath maintaining a sample temperature of from 92°–95° C. for 15–30 minutes. The time for inactivation of the protease enzyme is dependent upon the original enzyme concentration. Commercial alpha-amylase in powder form may be purified according to the same method by dissolving in a glycerol to water mixture of the preferred ratio as noted above. The PBAA is subsequently fractionated with ethanol. The PBAA is dissolved in a 5% sodium chloride solution and then made to 54.5%/V with ethanol discarding the insolubles precipitated. The ethanol content is then increased from 54.5% to 61.5% collecting the fraction of enzyme precipitated. These insolubles comprise 48–50% of the enzyme and is designated "fresh 80".

The fractionated PBAA (54.5–61.5%) is adsorbed on wheat-flour using a spray and blend technique. A Littleford mixer is equipped with a spray device. Dissolved PBAA is added to the reservoir of the spray device and the spray action activated. The mixing chamber is filled with flour then processed with concurrent spray and blending for about 15 minutes. A product of greater uniformity can be obtained by spraying for 15 minutes then interrupting the spraying and continuing the blending process for another 5–15 minutes.

While particular embodiments of this invention have been disclosed herein, it will be understood that various modifications may become apparent to those skilled in the art without departing from the spirit and scope of the invention which is defined by the appended claims.

TABLE I

Preliminary Baking Experiment Using Commercial Bacterial alpha-Amylase

| % Commercial Bacterial Alpha-Amylase | Dough Proof Time, min. | Bread Volume, c.c. | Instron (gm.) (Full Scale) | Comments on Bread Quality |
|---|---|---|---|---|
| Control (none) | 56.5 | 2,772.7 | 198.7 | Normal |
| 0.3 | 56.0 | Loaf Collapsed | — | Extremely Sticky Bread Crumb |
| 0.03 | 56.0 | Loaf Collapsed | — | Extremely Sticky Bread Crumb |
| 0.003 | 56.0 | 2,703.9 | 61.4 | Sticky |
| 0.0003 | 55.2 | 2,798.9 | 206.5 | V. sl. sticky |

TABLE II

Enzyme Potency of Various Sample of Commercial Bacterial Amylase

| Supplier | Sample Identification | Physical State | % Solids | Protease, HUT* | Amylase, D.U.* | Amylase to Protease Ratio, D.U.:HUT |
|---|---|---|---|---|---|---|
| 1. Enzyme Development Corporation | K-3896 | powder | 99.64 | 8,082.3 | 7,527.1 | 1:1.07 |
|  | K-3895 | powder | 97.35 | 73,189.5 | 85,606.1 | 1:0.85 |
|  | K-3829 | liquid | 71.91 | 5,405.0 | 149,005.7 | 1:0.04 |
| 2. Miles' Laboratories | HT-1000 | powder | 98.85 | 9,780.7 | 23,345.4 | 1:0.41 |
|  | HT-2000 | powder | 92.97 | 22,632.7 | 46,100.9 | 1:0.49 |
|  | HT-Concentrate | powder | 94.44 | 382,737.7 | 145,922.5 | 1:2.60 |
| 3. Rohm and Haas | Rhozyme H-39 | powder | 94.39 | 37,963.0 | 35,314.4 | 1:1.10 |
| 4. Fermco Biochemics | Veron F-25 | powder | 93.43 | 392.4 | 1,167.5 | 1:0.34 |
| 5. Wallerstein Company | WC-8 | powder | 98.37 | 24,355.2 | 25,414.2 | 1:10 |
|  | Fresh-N | powder | 93.47 | 212.2 | 229.0 | 1:0.93 |

TABLE III

Effects of Temperature and ph on the Inactivation of Protease Enzyme(s) in Rhozyme H-39 Preparation[1]

Residual Relative Protease Activity, %
Temperature, °C.

| pH | 40 | 50 | 60 | 70 |
|---|---|---|---|---|
| 9.10 | 105.8 | 108.9 | 87.20 | 10.6 |
| 8.52 | 106.6 | 110.9 | 81.9 | 12.0 |
| 7.50 | 104.1 | 110.4 | 80.5 | 7.1 |
| 6.50 | 110.7 | 106.9 | 77.8 | 3.8 |
| 5.50 | 109.1 | 107.4 | 77.3 | 3.5 |
| 3.70 | 94.8 | 80.1 | 10.0 | 0 |
| 4.00 | 50.7 | 14.9 | 0 | 0 |
| 3.50 | 30.8 | 6.9 | 0 | 0 |

TABLE IV

Effect of Time of Heating at 70° C. on the Inactivation of Protease Enzyme(s) in Rhozyme H-39 Preparation

| Time, Min. | Residual Relative Protease Activity, % |
|---|---|
| 0 | 100.0 |
| 5 | 14.4 |
| 15 | 0 |
| 20 | 0 |
| 30 | 0 |

TABLE V

The Effect of Concentration and Ionic Composition of Buffer Solutions on the Inactivation of Protease Enzyme(s) Present in the Commercial Alpha-Amylase

| Buffer Used | Residual Relative Protease Activity, % |
|---|---|
| Water | 0.5 |
| 0.1M Sodium Acetate | 1.0 |
| 0.5M Sodium Acetate | 1.2 |
| 1.0M Sodium Acetate | 41.3 |
| 0.5M Sodium Acetate | 1.2 |
| 0.5M Potassium Acetate | 55.2 |
| 0.5M Calcium Acetate | 97.1 |
| 0.5M Sodium Chloride | 0 |
| 0.5M Calcium Chloride | 12.0 |

TABLE VI

Effect of Sodium Chloride Concentration on the Stability of the Alpha-Amylase Enzyme During Heat Inactivation of Protease in Rhozyme H-39 Alpha-Amylase

| Concentration Sodium Chloride | Residual Relative Alpha-Amylase Activity, % |
|---|---|
| 0.1M | 84.8 |
| 0.3M | 94.0 |
| 0.5M | 100.0 |
| 0.8M | 100.0 |
| 1.0M | 100.0 |
| 1.5M | 92.0 |

TABLE VII

Comparative Effect of 0.20% CaSO$_4$, CaCl$_2$ and Ca(H$_2$PO$_4$)$_2$ on the Amylase Activity

| Source of Calcium ions | Concentration, % (W/V) | Temperature Used, °C. | Amylase Activity, D.U. |
|---|---|---|---|
| CaSO$_4$ . 2H$_2$O | 0.20 | 75 | 133,333.2 |
| CaCl$_2$ . H$_2$O | 0.20 | 75 | 18.750.0 |
| Ca(H$_2$PO$_4$)$_2$ . H$_2$O | 0.20 | 75 | 6,000.0 |

TABLE VIII

Effect of Temperature on the Enzymes When Thermally Treated with 0.0006M CaSO$_4$ (pH 6.50)

| Temperature, C. (30 min.) | NaCl, M | CaSO$_4$, M | Amylase, D.U./g. (as is) | Protease, HUT/g. (as is) |
|---|---|---|---|---|
| Control (no heat) | 0 | 0 | 133,333.2 | 361,457.5 |
| 75 | 0.8 | 0 | 85,714.2 | 1,228.6 |
| 75 | 0.8 | 0.0006 | 120,000.0 | 1,228.6 |
| 80 | 0.8 | 0 | 28,571.4 | 552.4 |
| 80 | 0.8 | 0.0006 | 66,666.6 | 709.5 |
| 97 | 0.8 | 0 | 4,285.7 | 0 |
| 97 | 0.8 | 0.0006 | 3,750.0 | 790.4 |

TABLE IX

Effect of CaSO4 Concentration on the Amylase Activity When Heated at ɸ75° C. for 30 Minutes

| Concentration of CaSO$_4$ . 2H$_2$O, M | Temperature °C. | Amylase, D.U./g. (as is) |
|---|---|---|
| Control (no heat) | Room Temp. | 133,333.2 |
| 0.0003 | 75 | 120,000.0 |
| 0.0006 | 75 | 120,000.0 |
| 0.0012 | 75 | 120,000.0 |
| 0.0030 | 75 | 63,157.8 |
| 0.0048 | 75 | 35,294.1 |
| 0.0060 | 75 | 33,333.3 |

TABLE X

Effect of Wheat Starch on the Amylase Activity When Heated at ɸ75° C.

| Treatment | NaCl, M | CaSO$_4$, M | Wheat Starch, % | Temperature, °C. | Amylase Activity, D.U. |
|---|---|---|---|---|---|
| Control (no heat) | 0 | 0 | 0 | Room T. | 133,333.2 |
| Enzyme Solution | 0.8 | 0 | 0 | 75 | 85,714.2 |
| Enzyme Solution | 0.8 | 0.0006 | 0 | 75 | 120,000.0 |
| Enzyme Solution | 0.8 | 0.0006 | 1.0 | 75 | 133,333.2 |
| Enzyme Solution | 0.8 | 0.0006 | 0 | 80 | 66,666.6 |
| Enzyme Solution | 0.8 | 0.0006 | 3.0 | 80 | 120,000.0 |
| Enzyme Solution | 0.8 | 0.0006 | 5.0 | 80 | 120,000.0 |

TABLE XI

Effect of Commercial Amylase Concentration on the Rate of Protease Inactivation When Treated at 75° C. (30 Min.)

| % Comm. Enzyme Concentration, as Received | *Amylase, D.U./g. Control(no heat) | *Amylase, D.U./g. Heated | *Protease, HUT/g. Heated | Amylase:Protease, D.U.:HUT/g. |
|---|---|---|---|---|
| Control (no heat) | — | — | 2,697.6 | — |
| 1.0 | 100,000.0 | 93,750.0 | None | 93,750.0:0 |
| 5.0 | 92,307.6 | 80,000.0 | 66.7 | 1,199:1 |
| 10.0 | 92,307.6 | 85,714.2 | 111.7 | 767:1 |
| 20.0 | 100,000.0 | 93,750.0 | 245.0 | 383:1 |
| 30.0 | 107,142.8 | 100,000.0 | 420.0 | 238:1 |
| 40.0 | 100,000.0 | 100,000.0 | 578.3 | 174:1 |
| 50.0 | 85,714.2 | 85,714.2 | 878.3 | 98:1 |
| 70.0 | 83,333.2 | 83,333.2 | 1,286.7 | 65:1 |
| Mean (1%–70%) | 95,100.7 | 90,282.7 | — | — |

*Enzyme activity expressed on per gram of commercial liquid enzyme.

TABLE XII

Bread Formula Used For Baking Studies

| | Weight, % |
|---|---|
| Sponge Ingredients | |
| Flour | 65.00 |
| Yeast | 2.00 |
| Yeast Food | 0.50 |
| Tap Water | 60.00 |
| Dough Ingredients | |
| Flour | 35.00 |
| Salt | 2.25 |
| Corn Sugar (dry) | 10.00 |
| Shortening | 3.00 |
| Extram C | 2.00 |
| Improved Paniplus | 0.30 |
| Calcium Sulfate | 0.47 |
| Tap Water as needed for proper absorption | |

TABLE XIII

Effect of the Level of Purified Alpha-Amylase on Rate of Bread Firming

| Concentration of Purified Alpha-Amylase, D.U./800 g. of Flour (14% M.B.) | Instron Firmness Values (g. Full Scale) After Storage for Days | | |
|---|---|---|---|
| | 1 | 3 | 6 |
| 0 | 104.1 | 184.1 | 294.6 |
| 18.0 | 107.2 | 180.5 | 286.3 |
| 36.1 | 118.7 | 185.8 | 251.4 |
| 54.1 | 109.6 | 181.2 | 243.1 |
| 72.2 | 114.5 | 191.. | 236.1 |

TABLE XIV

The Effect of Different Levels of Purified Alpha-Amylase Used in Combination with 0.5 Percent Calcium Stearate[1] on the Rate of Bread Firming

| Concentration of Purifed Alpha-Amylase, D.U./800 g. of Flour (14% M.B.) | | Instron Firmness Values (g. Full Scale) After Storage for Days | | |
|---|---|---|---|---|
| | | 1 | 3 | 6 |
| No Enzyme, | 0% Calcium Stearate | 104.1 | 184.1 | 294.6 |
| No Enzyme, | 0.5% Calcium Stearate | 98.0 | 158.2 | 223.3 |
| 18.0 D.U. Enzyme, | 0.5% Calcium Stearate | 93.9 | 138.9 | 188.4 |
| 36.1 D.U. Enzyme, | 0.5% Calcium Stearate | 103.8 | 130.5 | 185.5 |
| 54.1 D.U. Enzyme, | 0.5% Calcium Stearate | 92.8 | 124.2 | 174.1 |
| 72.2 D.U. Enzyme, | 0.5% Calcium Stearate | 91.7 | 115.2 | 138.0 |
| 130 D.U. Enzyme, | 0.5% Calcium Stearate | 99.3 | 117.5 | 119.3 |
| 150 D.U. Enzyme, | 0.5% Calcium Stearate | 97.5 | 112.5 | 111.2 |

TABLE XV

Effect of the Purifed Alpha-Amylase Concentration when Used in Combination with 0.5% Calcium Stearate on the Rate of Bread Firming Over a Six-Day Storage Period

| Concentration of Purified Alpha-Amylase, D.U./800g. of Four (14% M.B.) | | Increase in Instron Value Per Day Over 6-Day Storage Period |
|---|---|---|
| No Enzyme | 0% Calcium Stearate | 31.8 |
| No Enzyme | 0.5% Calcium Stearate | 20.9 |
| 18.0 D.U. Enzyme, | 0.5% Calcium Stearate | 15.8 |
| 36.1 D.U. Enzyme, | 0.5% Calcium Stearate | 13.6 |
| 54.1 D.U. Enzyme, | 0.5% Calcium Stearate | 13.6 |
| 72.2 D.U. Enzyme, | 0.5% Calcium Stearate | 7.7 |

TABLE XVI

Effect of Purified Alpha-Amylase plus 0.5 Percent Calcium Stearate on the Moisture Content of Bread

| Bread Additive Used | | Moisture Content of Bread, % After Storage Day | |
|---|---|---|---|
| Purified Alpha-Amylase | Calcium Stearate | 1 | 6 |
| None | None | 36.1 | 35.8 |
| None | 0.5% | 35.5 | 35.5 |
| 54.1 D.U. | None | 36.0 | 36.1 |
| 54.1 D.U. | 0.5% | 35.7 | 35.8 |

TABLE XVII

Effect of the Purified Alpha-Amylase Concentration When Used in Combination with 0.5% Calcium Stearate on the Loaf Quality

| Treatment Enzyme, D.U. + Surfactant, % | | | Proof Time, min. | Loaf Volume, cu. in. | Evaluation of Bread Quality[1] |
|---|---|---|---|---|---|
| 0 | + | 0 | 61.7 | 175.0 | normal |
| 0 | + | 0.5 | 61.5 | 176.5 | normal |
| 18.0 | + | 0.5 | 59.7 | 173.8 | normal |
| 36.1 | + | 0.5 | 62.0 | 175.8 | increasing tenderness |
| 54.1 | + | 0.5 | 61.3 | 174.5 | increasing tenderness |
| 72.2 | + | 0.5 | 61.3 | 175.5 | increasing tenderness |
| 90 | + | 0.5 | 57.2 | 172.7 | v. sl. gummy |
| 110 | + | 0.5 | 57.7 | 173.7 | sl. gummy |
| 130 | + | 0.5 | 58.4 | 171.8 | gummy |
| 150 | + | 0.5 | 58.5 | 173.3 | gummy |

TABLE XVIII

Effect of Varying Levels of the Purified Amylase and Calcium Stearate on the Rate of Bread Firming and Loaf Quality

| Enzyme Concentration D.U. | Calcium Stearate Concentration % | Instron Firmness Values (Mode Value), After Storage for Days | | | Proof Time, min. | Loaf Volume cu. in. | Grain | Color |
|---|---|---|---|---|---|---|---|---|
| | | 1 | 3 | 6 | | | | |
| 45.12 | 0 | 104.3 | 190.3 | 283.2 | 55.5 | 173.5 | fine | bright |
| 54.15 | 0 | 112.1 | 172.3 | 284.3 | 58.5 | 177.0 | sl. open | bright |
| 63.17 | 0 | 123.3 | 175.9 | 307.9 | 58.5 | 174.0 | open | v. sl. dull |
| 45.12 | 0.25 | 96.3 | 157.8 | 201.5 | 60.0 | 175.0 | fine | bright |
| 54.14 | 0.25 | 95.5 | 146.1 | 179.9 | 57.0 | 175.5 | sl. open | bright |
| 63.17 | 0.25 | 110.4 | 150.8 | 180.1 | 59.0 | 173.8 | sl. open | bright |
| 45.12 | 0.50 | 85.0 | 126.4 | 175.7 | 58.0 | 176.2 | fine | bright |
| 54.14 | 0.50 | 88.7 | 125.7 | 146.2 | 58.0 | 174.8 | sl. open | bright |
| 63.17 | 0.50 | 88.8 | 104.9 | 150.2 | 58.5 | 177.2 | sl. open | bright |

TABLE XIX

Effect of Varying Levels of Calcium Stearate in Combination with 54 D.U. of Purified Amylase on the Rate of Bread Firming

| Enzyme Concentration D.U. | Calcium Stearate Concentration % | Instron Firmness Values (Mode Value), After Storage for Days | | |
|---|---|---|---|---|
| | | 1 | 3 | 6 |
| 54 | 0.5 | 112.8 | 153.5 | 204.9 |
| 54 | 0.8 | 106.2 | 153.4 | 191.3 |
| 54 | 1.0 | 111.6 | 138.8 | 162.3 |
| 54 | 2.0 | 123.1 | 144.2 | 155.3 |

TABLE XX

Comparative Effects of 90-150 D.U. of Amylase 30 0.5% Calcium Stearate System and 0.5%-2.0% Calcium Stearate + 54 D.U. Amylase System on Bread Loaf Quality and Bread Firming

| Concentration of Purified Alpha Amylase, D.U. | Concentration of Calcium Stearate, % (Flour Basis) | Instron Firmness Values (Mode Value), After Storage for Days | | | Proof Time, min. | Loaf Volume, cu. in | Evaluation of Bread Quality |
|---|---|---|---|---|---|---|---|
| | | 1 | 3 | 6 | | | |
| 90 | 0.50 | 108.2 | 142.4 | 170.9 | 57.2 | 172.7 | v.sl. gummy |
| 110 | 0.50 | 106.0 | 127.7 | 140.9 | 57.7 | 173.7 | sl. gummy |

TABLE XX-continued

Comparative Effects of 90-150 D.U. of Amylase 30 0.5% Calcium Stearate System and 0.5%-2.0% Calcium Stearate + 54 D.U. Amylase System on Bread Loaf Quality and Bread Firming

| Concentration of Purified Alpha Amylase, D.U. | Concentration of Calcium Stearate, % (Flour Basis) | Instron Firmness Values (Mode Value), After Storage for Days | | | Proof Time, min. | Loaf Volume, cu. in | Evaluation of Bread Quality |
|---|---|---|---|---|---|---|---|
| | | 1 | 3 | 6 | | | |
| 130 | 0.50 | 94.3 | 117.5 | 119.3 | 58.4 | 171.8 | gummy |
| 150 | 0.50 | 97.5 | 112.5 | 111.2 | 58.5 | 173.3 | gummy |
| 54 | 0.50 | 112.8 | 153.5 | 204.9 | 57.5 | 173.5 | normal |
| 54 | 0.80 | 106.2 | 153.4 | 191.3 | 58.7 | 173.5 | normal |
| 54 | 1.00 | 111.6 | 138.8 | 162.3 | 58.3 | 171.2 | normal |
| 54 | 2.00 | 123.1 | 144.2 | 155.3 | 60.3 | 158.3 | normal |

TABLE XXI

Effect of Various Commercial Surfactants With and Without 54 D.U. of Purified Amylase on the Rate of Bread Firming

| Surfactant Used | Concentration of Surfactant, % | Concentration of Purified Amylase, D.U. | Instron Firmness Value (Mode Value), after Storage for Days | | |
|---|---|---|---|---|---|
| | | | 1 | 3 | 6 |
| 0 | 0 | 0 | 106.4 | 197.6 | 239.1 |
| 0 | 0 | 54 | 114.4 | 203.2 | 210.7 |
| SSL | 0.5 | 0 | 92.6 | 148.9 | 178.3 |
| SSL | 0.5 | 54 | 78.6 | 123.0 | 144.4 |
| CSL | 0.5 | 0 | 98.4 | 143.7 | 187.1 |
| CSL | 0.5 | 54 | 83.4 | 132.8 | 147.8 |
| Soft Touch | 0.5 | 0 | 94.4 | 160.7 | 199.3 |
| Soft Touch | 0.5 | 54 | 87.6 | 141.9 | 170.2 |

TABLE XXII

Effect of Various Commercial Surfactants With and Without 54 D.U. of Purified Amylase on the Rate of Bread Firming GROUP II

| Surfactant Used | Concentration of Surfactant, % | Concentration of Purified Amylase, D.U. | Instron Firmness Value (Mode Value), after Storage for Days | | |
|---|---|---|---|---|---|
| | | | 1 | 3 | 6 |
| 0 | 0 | 0 | 108.1 | 212.2 | 281.7 |
| 0 | 0 | 54 | 117.2 | 223.0 | 277.3 |
| Ca Stearate | 0.5 | 0 | 104.7 | 167.6 | 223.8 |
| Ca Stearate | 0.5 | 54 | 88.3 | 129.3 | 160.0 |
| SMG | 0.5 | 0 | 94.4 | 159.6 | 210.4 |
| SMG | 0.5 | 54 | 92.7 | 155.6 | 192.0 |
| EMG | 0.5 | 0 | 104.3 | 203.4 | 288.6 |
| EMG | 0.5 | 54 | 101.5 | 193.8 | 244.1 |

TABLE XXIII

Effect of Various Commercial Surfactants With and Without 54 D.U. of Purified Amylase on the Rate of Bread Firming GROUP III

| Surfactant used | Concentration of Surfactant, % | Concentration of Purified Amylase, D.U. | Instant Firmness Value (Mode Value), after Storage for Days | | |
|---|---|---|---|---|---|
| | | | 1 | 3 | 6 |
| 0 | 0 | 0 | 107.7 | 180.3 | 294.5 |
| 0 | 0 | 54 | 100.4 | 170.5 | 258.7 |
| GMS-90 | 0.5 | 0 | 99.7 | 144.7 | 194.9 |
| GMS-90 | 0.5 | 54 | 81.6 | 119.2 | 155.3 |
| P-60 | 0.5 | 0 | 107.1 | 187.0 | 248.9 |
| P-60 | 0.5 | 54 | 102.5 | 173.2 | 229.8 |
| FFA | 0.5 | 0 | 112.9 | 171.6 | 259.5 |
| FFA | 0.5 | 54 | 99.9 | 139.2 | 174.8 |

TABLE XXIV

Effect of a Combination of 54 D.U. of Purified Bacterial Amylase plus Commercial Surfactants on the Rate of Firming During a Six-Day Storage Period

| Surfactant Used | Concentration of Surfactant, % | Concentration of Purified Amylase D.U./800 g. of Flour | Increase in Instron Value Per Day Over Six Days Storage Period |
|---|---|---|---|
| 0** | 0 | 0 | 27.4 |
| 0** | 0 | 54 | 23.0 |
| SSL | 0.5 | 54 | 11.0 |
| Ca Stearate* | 0.5 | 54 | 12.0 |
| GMS-90 | 0.5 | 54 | 12.3 |
| FFA* | 0.5 | 54 | 12.5 |
| Soft Touch | 0.5 | 54 | 13.8 |
| CSL | 0.5 | 54 | 14.8 |
| SMG | 0.5 | 54 | 19.3 |
| P-60 | 0.5 | 54 | 21.2 |
| EMG | 0.5 | 54 | 23.8 |

*Not commercial surfactants.
**Mean of Values obtained in Groups I, II, III.

TABLE XXV

| Commercial Surfactant | Acts Primarily on | | Descriptive Term Used to Identify Primary Function | Where Found in Bread (Bound) | |
|---|---|---|---|---|---|
| | Gluten | Starch | | Gluten | Starch |
| SSL | Yes | Yes | Crumb Softener Dough Strengthener | Some | Most |
| CSL | Yes | Yes | Crumb Softener Dough Strengthener | Some | Most |
| GMS-90 | No | Yes | Crumb Softener | Trace | Most |
| SMG | Yes | Yes | Crumb Softener Dough Strengthener | Some | Most |
| P-60 | Yes | No | Dough Strengthener | Most | Some |
| EMG | Yes | No | Dough Strengthener | Most | Some |
| Ca Stearate | No | Yes | Crumb Softener | Some | Most |
| FFA | No | Yes | Crumb Softener | Some | Most |

TABLE XXVI

Effect of Various Organic Solvents on the Precipitation of Bacterial Alpha-Amylase from Dilute Aqueous Solutions

| Organic Solvent Used | Ratio of Enzyme Solution to Solvent, ml. | Enzyme Concentration, mg./ml. | Aliquot Used for Assay, ml. | % Relative Activity Remaining After Indicated Treatment |
|---|---|---|---|---|
| Bacterial Amylase-no Heat Treatment | — | 20/4 | 5 ml. (24D.U.) | 100.0 (Soln.) |
| Bacterial Amylase-Heat Treated | — | 20/4 | " | 100.0 (Soln.) |
| Acetone | 1:4 | 20/4 | " | 100.0 (ppt.) |
| Methanol | 1:4 | 20/4 | " | 100.0 (ppt.) |
| Ethanol | 1:4 | 20/4 | " | 100.0 (ppt.) |
| Isopropanol | 1:4 | 20/4 | " | 100.0 (ppt.) |

TABLE XXVII

Effect of Various Levels of Acetone on the Precipitation of Bacterial Alpha-Amylase from Aqueous Solutions

| Enzyme Solution:Acetone/ml. | Enzyme Concentration Used, mg./ml. | % Relative Activity Remaining After Acetone Precipitation |
|---|---|---|
| Control Enzyme Solution | 20/20 | 100.0 |
| 1:05 | 20/20 | 0 |
| 1:0.8 | 20/20 | 28.8 |
| 1:1 | 20/20 | 90.3 |
| 1:2 | 20/20 | 91.5 |
| 1:3 | 20/20 | 90.3 |
| 1:4 | 20/20 | 91.5 |

TABLE XXVIII

Comparative Anti-Firming Effect of Bacterial Alpha-Amylase on Starch Carriers During a Six-Day Storage Period

| Treatment | Enzyme Concentration, D.U./800 g. Flour | Calcium Stearate Concentration Used, % | Instron Firmness Value (Mode Value), After Days 1 | 3 | 6 |
|---|---|---|---|---|---|
| Purified Enzyme Solution | 60.0 | 0.5 | 101.8 | 160.5 | 201.7 |
| Purified Enzyme on Starch Carrier | 60.0 | 0.5 | 106.8 | 168.5 | 220.8 |

TABLE XXIX

Stabilizing Effect of Calcium Sulfate, Wheat Starch and Stabilize the Bacterial Amylase in Tap Water

| Formula Ingredient | Time Required for the Formation of Desired Color Complex*, min. |
|---|---|
| 1. Bacterial Alpha-Amylase in Deionized Water (control) | 11.0 |
| 2. Calcium Sulfate (Terra Alba) | Color complex not obtained, even after 18 hours of digestion |
| 3. Wheat Starch | |
| 4. Wheat Flour | 7.0 |

*One DU represents the enzyme activity required to dextrinize 20 mg of soluble starch substrate in 30 minutes at 30° C. and pH 6.50. It is reported as DU per gram of enzyme.

TABLE XXX

Minimum Amount of Flour Required to Stabilize the Bacterial Amylase in Tap Water

| Flour Concentration in Tap Water, % | Enzyme Activity Relative Gain, % | Relative Loss, % |
|---|---|---|
| 0 | 0 | 100.0 |
| 0.2 | — | 6.4 |
| 0.6 | 0 | — |
| 1.0 | 12.9 | — |
| 2.0 | 38.7 | — |
| 4.0 | 41.9 | — |

TABLE XXXI

Effect of pH of a Ferrous Sulfate Solution on the Bacterial Amylase Activity

| pH of a Ferrous Sulfate plus Tap Water System | Ferrous Sulfate Concentration, mg./500 ml. | Bacterial Amylase Activity, DU/g. (as is) |
|---|---|---|
| 1. Enzyme in Deionized Water (pH 6.50) | 0 | 100,000.0 |
| 2. pH 8.00 tap water | 5.0 | 100,000.0 |
| 3. pH 7.00 tap water | 5.0 | 100,000.0 |
| 4. pH 6.50 tap water | 5.0 | 75,000.0 |
| 5. pH 5.80 tap water | 5.0 | 15,883.9 |

TABLE XXXII

Effect of Ferrous Sulfate Concentration in Tap Water on the Stability of the Bacterial Amylase Activity

| | Ferrous Sulfate Concentration, mg./100 ml. of Tap Water | pH of Test System | Enzyme Concentration, DU/100 ml. | Residual Enzyme Activity, DU/g. |
|---|---|---|---|---|
| 1. Enzyme in Deionized Water, no FeSO4 | adjusted to 8.60 | | 2000.0 | 100,000.0 |
| 2. | 0.1 | 8.60 | 2000.0 | trace |
| 3. | 0.2 | 8.60 | 2000.0 | 91,534.6 |
| 4. | 0.3 | 8.60 | 2000.0 | 100,000.0 |
| 5. | 0.5 | 8.60 | 2000.0 | 100,000.0 |
| 6. | 1.0 | 8.60 | 2000.0 | 100,000.0 |

TABLE XXXIII

Comparative Stabilizing Effects of Enriched and Unenriched Flour on the Bacterial Alpha-Amylase

| Type of Flour Added to Tap Water | Flour Concentration g./100 ml. | pH of Test System | Residual Bacterial Amylase Activity, DU/g. |
|---|---|---|---|
| 1. Enriched Flour | 20.0 | 5.85 | 138,478.8 |
| 2. Unenriched Flour | 20.0 | 5.85 | 138,478.8 |

TABLE XXXIV

EFFECT OF pH AND GLYCEROL - WATER RATIO ON THE ENZYME ACTIVITY OF COMMERCIAL POWDER ENZYMES

| Commercial Enzyme | pH | Glycerol To Water Ratio | Time at 92°-95° C. | Amylase, DU/g Before | After | Protease, HUT/g Before | After |
|---|---|---|---|---|---|---|---|
| HT-1000 | 7.50–9.00 | 2.33:1 | 15 | 24,000.0 | 23.529.4 | 9,808.0 | trace |
| Enzeco | 7.50–9.00 | 2.33:1 | 15 | 75,000.0 | 75,000.0 | 28,095.2 | trace |
| HT-1000 | 7.50–9.00 | 2.33:1 | 30 | 24,000.0 | 23,529.4 | 9,908.0 | trace |
| Enzeco | 7.50–9.00 | 2.33:1 | 30 | 75,000.0 | 75,000.0 | 28,095.2 | trace |

TABLE XXXV

EFFECT OF PROTEASE-FREE BAA PREPARED AT 75° C. AND AT 92°-95° C. ON BREAD AND CRUMB CHARACTERISTICS

| Thermal Treatment to obtain Protease-Free BAA | Instron 6th Day | Loaf Quality Scoring[1] Softness[2] | Gumminess[3] | Grain[4] | Crumb[5] |
|---|---|---|---|---|---|
| Control, no PBAA | 214.0 | 3 | 5 | 4 | 4 |
| 75° C. procedure described | 156.0 | 4 | 2 | 2 | 2 |
| 92°–95° C. (heated glycerol solution) | 165.0 | 4 | 3 | 3 | 3 |

[1] Bread Laboratory (baking test of 8/1/78)
[2] 1-firm, 5-soft
[3] 5-not gummy, 1-gummy
[4] 5-close, 1-open
[5] 5-high crumb quality, 1-low

TABLE XXXVI

Preliminary PBAA Fractionation Using Methanolic - 5% NaCl Mixtures

| Ratio of MeOH to 5% NaCl Solution (v:v) | Qualitative Extend of Enzyme Precipitation |
|---|---|
| 9.5:0.5 (95.0%/v.) | precipitated, none in supernatant |
| 3.0:1.0 (75.0%/v.) | precipitated, none in supernatant |
| 2.0:1.0 (66.7%/v.) | mostly precipitated, some in supernatant |
| 1.0:1.0 (50.0%/v.) | trace amount precipitated, mostly in supernatant |

TABLE XXXVII

Effect of Various Enzyme Fractions Isolated From Maxamyl PBAA on Bread Quality

| Variable | Instron Firmness Value (Day 6) | Softness | Gumminess | Grain | Crumb |
|---|---|---|---|---|---|
| 1. 0.3% SSL + 1% Panatex, no PBAA (control) | 215 | 2.6 | 4.1 | 3.7 | 3.5 |
| 2. PBAA, as is | 172 | 3.8 | 2.8 | 2.8 | 2.8 |
| 3. 60 + 50 fraction (54.5%) | 186 | 3.4 | 2.9 | 2.6 | 2.4 |
| 4. 70 + 50 fraction (58.3%) | 190 | 3.1 | 3.2 | 2.8 | 2.8 |
| 5. 80 + 50 fraction (61.5%) | 176 | 3.2 | 3.2 | 3.6 | 3.4 |
| 6. 90 + 50 fraction (64.3%) | 182 | 3.7 | 2.6 | 2.5 | 2.5 |
| 7. 100 + 50 fraction (66.%) | 178 | 3.8 | 3.0 | 2.4 | 2.4 |

Data above represents the mean of twelve loaves of bread, two independent baking experiments, two different flour shipments, involving six separate preparations of the same variable. The enzyme fractions were added on same activity basis (75 DU) in combination with same surfactant system as in (1.).

TABLE XXXVIII

Relative Amount of PBAA Precipitated by Progressively Increasing the Alcohol Concentration of the Enzyme Solution

| Enzyme Fraction Precipitated with MeOH + 5% NaCl (v + v) | Ratio of MeOH:5% NaCl (v:v) | % of the Original Enzyme Activity |
|---|---|---|
| Stepwise Precipitation: | | |
| 50 + 50 precipitate | 1:1 (50.0%/v.) | 0–0.5 |
| 60 + 50 precipitate | 1.2:1 (54.5%/v.) | 11.0 |
| 70 + 50 precipitate | 1.4:1 (58.3%/v.) | 37.3 |
| 80 + 50 precipitate | 1.6:1 (61.5%/v.) | 18.7 |
| 90 + 50 precipitate | 1.8:1 (64.3%/v.) | 12.7 |
| 100 + 50 precipitate | 2:1 (66.7%/v.) | 9.3 |
| Enzyme Solution | | 10.0–10.5 |

TABLE XXXIX

Bacterial Alpha-Amylase Description and Usage Levels

| Enzymes Present | Activity As Received (BAA) | Modified*** (PBAA) |
|---|---|---|
| In Commercial Blend* | | |
| Amylase (DU/gram) | 32,000 | 32,000 |
| Protease (HUT/gram) | 5,130 | trace |
| In Flour** | | |
| At low activity level ($C_1$): | | |
| Amylase (DU/800 grams) | 75 | 75 |
| Protease (HUT/800 grams) | 12 | trace |
| At high activity level ($C_2$): | | |
| Amylase (DU/800 grams) | 150 | 150 |
| Protease (HUT/800 grams) | 24 | trace |

*The commercial enzyme (BAA), identified as WC-8, Lot No. K7K 653 (1978, was supplied by the G.B. Fermentation Industries Inc., Des Plains, Illinois 60016. This commercial enzyme was produced from *Bacillus subtilis* organisms, and modified at the Rye R & D Laboratories to produce PBAA.
**The unmodified and modified enzymes were added to the flour as described.
***Modified without the use of alcohol (to remove undesirable components).

What is claimed is:
1. A method comprising the steps of:
providing a solution of alpha-amylase enzyme and protease enzyme;
adjusting the solution with about 0.0006 M calcium sulphate and about 0.8 M sodium chloride to a pH of about 6.5;
heating the solution to about 75° C.;

adding to the solution from 1-3% wheat starch and the mixture adjusted to a pH of about 6.5; and holding the solution from 15-30 minutes to inactivate the protease enzyme activity.

2. A method comprising the steps of:
providing an alpha-amylase enzyme free of protease activity; and
adding the alpha-amylase to chlorinated tap water in the presence of at least 2.0-5.0% wheat flour.

3. The method of claim 2 wherein the water has a pH of from 3.50-6.10.

4. A method for the introduction of alpha-amylase to chlorinated tap water comprising the step of:
adding the alpha-amylase which is free of protease activity to the tap water in the presence of at least about 0.3 mg. of ferrous sulfate per 100 ml. water at a pH above about 6.50.

5. A method of introducing a dry enzyme concentrate to wheat flour comprising the steps of:
suspending wheat starch in acetone,
adding protease-free alpha-amylase to the acetone,
separating the starch from the acetone, and
blending the separated starch with wheat flour.

6. The method of claim 5 wherein there is provided about 3405 DU alpha-amylase per 100 lbs. of flour.

7. A method of inactivation of protease enzyme in a mixture comprising alpha-amylase enzyme and glycerol and water comprising the steps of:
adjusting the mixture to a pH from 7.50-9.50;
adjusting the ratios of glycerol to water from 6.0-1.0:1 by weight; and
heating the mixture to a temperature of from 92°-95° C. for a time sufficient to inactivate the protease enzyme.

8. The method of claim 7 wherein the mixture is held from 15-30 minutes.

9. The mixture of claim 7 wherever the ratio is 2.33:1.

10. In a mixture comprising alpha-amylase enzyme, protease enzyme, glycerol and water, a method of inactivation of the protease enzyme activity while retaining the alpha-amylase activity comprising the steps of:
adjusting the mixture to a pH from 7.50-9.50 and a glycerol to water ratio of from 6.0-1.0:1 by weight, heating the mixture from 92°-95° C., and
holding the heated mixture from 15-30 minutes until the protease enzyme is inactivated.

11. The method of claim 10 wherein the ratio is 2.33:1.

12. In a mixture of alpha-amylase enzyme and protease enzyme and glycerol and water, a method of inactivation of the protease enzyme comprising the step of:
heating the mixture to a temperature of from 92°-95° C. at a pH from 7.50-9.50 and at a glycerol to water ratio of from 6.0-1.0:1 for a time sufficient to inactivate the protease enzyme.

13. A method of introducing a dry enzyme concentrate to wheat flour comprising the steps of:
suspending wheat starch in acetone,
adding protease-free alpha-amylase to the acetone,
separating the starch from the acetone, and
blending the separated starch with wheat flour, wherein the protease-free alpha-amylase is made according to the method of claims 7, 10 or 12.

14. The method of claims 7, 10 or 12 wherein the alpha-amylase and protease is provided as a powder.

15. The method of claims 7, 10 or 12 wherein the alpha-amylase is selected from the group consisting of *Bacillus subtilis* and *Bacillus sterothermophilis*.

16. The method of claims 7, 10 or 12 after inactivation of the protease enzyme, further including the steps of:
adding the alpha-amylase to a NaCl solution, and
fractionating the alpha-amylase by the addition of alcohol thereby precipitating a fraction of the alpha-amylase.

17. The method of claim 16 wherein the NaCl solution is about a 5% solution.

18. The method of claim 16 wherein the alcohol is a short chain alcohol.

19. The method of claim 18 wherein the alcohol is selected from the group consisting of methanol and ethanol.

20. The method of claim 16 wherein the alpha-amylase fraction is that precipitated by increasing the alcohol content from 50% to 66.7%.

21. The method of claim 20 wherein the content is from 50-64.3%.

22. The method of claim 20 wherein the content is from 50-61.5%.

23. The method of claim 20 wherein the content is from 50-58.3%.

24. The method of claim 20 wherein the content is from 50-54.5%.

25. The method of claim 20 wherein the content is from 54.5-61.5%.

26. The method of claim 20 wherein the content is from 54.5-58.3%.

27. The method of claim 20 wherein the content is from 58.3-61.5%.

28. The method of claim 16 wherein the NaCl solution contains wheat flour.

29. The method of claim 16 wherein the solution contains wheat flour.

30. The method of claim 16 further including the steps of adsorbing the desired fraction of PBAA on a flour carrier.

31. A method of fractionating modified alpha-amylase, wherein the modified alpha-amylase is prepared according to the method of claim 7, 10 or 12, comprising the steps of:
adding the modified alpha-amylase to about 50% alcohol solution containing NaCl,
increasing the alcohol to about 54.5% thereby precipitating an undesired fraction;
separating the undesired fraction, and
increasing the alcohol to about 61.5% thereby precipitating a desired fraction (54.5-61.5%) of modified alpha-amylase.

32. A dough comprising a combination of:
flour;
water;
from 0.5-2.0% calcium stearate; and
from 18-150 DU of purified alpha-amylase per about 800 grams of said flour, said purified alpha-amylase prepared according to claim 7, 10 or 12.

33. The dough of claim 32 wherein the purified alpha-amylase is present in from 45-150 DU.

34. The dough of claim 33 wherein the purified alpha-amylase is present in from 90-150 DU.

35. The dough of claim 34 wherein the purified alpha-amylase is present from 45-72 DU.

36. The dough of claim 32 wherein the calcium stearate concentration is from 0.5-1.0%.

37. The dough of claim 36 wherein the calcium stearate concentration is about 0.5%.

38. The dough of claim 32 wherein the calcium stearate concentration is about 1.0% and about 54 DU of purified enzyme is present.

39. The dough of claim 32 wherein the calcium stearate concentration is about 1.0% and from 90–100 DU or purified enzyme is present.

40. A dough comprising in combination:
a predetermined amount of flour;
chlorinated tap water;
a predetermined amount of surfactant weighing not in excess of 2.0% of the weight of said predetermined amount of flour, wherein said surfactant is selected from the group consisting of sodium stearoyl-2-lactylate, calcium stearate, glycerol monostearate, calcium stearoyl-2-lactylate and succinylated monoglyceride; and bacterial alpha-amylase completely free of detectable protease activity introduced to said dough in a predetermined amount not in excess of 150 DU per 800 grams of said predetermined amount of flour on a carrier comprising a portion of said flour, wherein the amount of surfactant and alpha-amylase combined is sufficient to retard firming of the product made from said dough, and wherein said alpha-amylase is prepared according to the method of claim 7, 10 or 12.

41. A dough comprising in combination:
a predetermined amount of flour;
chlorinated tap water;
a predetermined amount of surfactant weighing not in excess of 2.0% of the weight of said predetermined amount of flour, wherein said surfactant is selected from the group consisting of sodium stearoyl-2-lactylate, calcium stearate, glycerol monostearate, calcium stearoyl-2-lactylate and succinylated monoglyceride; and bacterial alpha-amylase completely free of detectable protease activity introduced to said dough in a predetemined amount not in excess of 150 DU per 800 grams of said predetermined amount of flour on a carrier comprising a portion of said flour wherein the amount of surfactant and alpha-amylase combined is sufficient to retard firming of the product made from said dough.

42. The dough of claim 41 wherein said predetermined amount of alpha-amylase is about 54 DU per 800 grams of said predetermined amount of flour.

43. The dough of claim 41 wherein the alpha-amylase is fractionated.

44. The dough of claim 41 wherein the alpha-amylase is produced by *Bacillus subtilis*.

45. The dough of claim 41 wherein said predetermined amount of surfactant is present from 0.25–2.0% of the weight of said predetermined amount of flour.

46. The dough of claim 41 wherein said predetermined amount of alpha-amylase is present from 18–150 DU per 800 grams of said predetermined amount of flour.

47. The dough of claim 41 wherein said dough is a bread dough.

48. The dough of claim 41 wherein said dough is a yeast-raised donut dough.

* * * * *

UNITED STATES PATENT AND TRADEMARK OFFICE
CERTIFICATE OF CORRECTION

PATENT NO. : 4,299,848

DATED : November 10, 1981

INVENTOR(S) : Vincent A. De Stefanis-Earl W. Turner

It is certified that error appears in the above—identified patent and that said Letters Patent is hereby corrected as shown below:

Column 5, lines 55-56, change "0.1M" to --1.0M--;

Column 18, line 34, delete "suspected.";

Column 18, line 49, change "Mexamyl" to --Maxamyl--.

Signed and Sealed this

Twenty-seventh Day of July 1982

[SEAL]

Attest:

Attesting Officer

GERALD J. MOSSINGHOFF

Commissioner of Patents and Trademarks